United States Patent
Harris et al.

(10) Patent No.: US 10,828,031 B2
(45) Date of Patent: Nov. 10, 2020

(54) SURGICAL STAPLER WITH ELASTICALLY DEFORMABLE TIP

(71) Applicant: ETHICON LLC, Guaynabo, PR (US)

(72) Inventors: Jason L. Harris, Lebanon, OH (US); Ryan Bledsoe, Cincinnati, OH (US); Gregory J. Bakos, Mason, OH (US); Joseph P. Schowalter, South Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 627 days.

(21) Appl. No.: 15/435,573

(22) Filed: Feb. 17, 2017

(65) Prior Publication Data
US 2018/0235609 A1     Aug. 23, 2018

(51) Int. Cl.
| | | |
|---|---|---|
| A61B 17/072 | (2006.01) | |
| A61B 17/00 | (2006.01) | |
| A61B 90/00 | (2016.01) | |
| A61B 17/29 | (2006.01) | |
| A61B 17/32 | (2006.01) | |

(52) U.S. Cl.
CPC ...... *A61B 17/07207* (2013.01); *A61B 17/072* (2013.01); *A61B 2017/0046* (2013.01); *A61B 2017/00964* (2013.01); *A61B 2017/07214* (2013.01); *A61B 2017/07257* (2013.01); *A61B 2017/07271* (2013.01); *A61B 2017/2929* (2013.01); *A61B 2017/2946* (2013.01);
(Continued)

(58) Field of Classification Search
CPC ...... A61B 17/07207; A61B 2090/0807; A61B 2017/0046; A61B 2017/00964; A61B 2017/07214; A61B 2017/07257; A61B 2017/07271; A61B 2017/2929; A61B 2017/2946; A61B 2017/320044
USPC .................. 227/180.1, 19, 151, 152
See application file for complete search history.

(56) References Cited

U.S. PATENT DOCUMENTS

| | | | |
|---|---|---|---|
| 4,805,823 A | | 2/1989 | Rothfuss |
| 5,014,899 A | * | 5/1991 | Presty ............. A61B 17/07207 227/151 |

(Continued)

FOREIGN PATENT DOCUMENTS

| | | |
|---|---|---|
| EP | 2 772 202 A2 | 9/2014 |
| WO | WO 2004/096057 A2 | 11/2004 |

(Continued)

OTHER PUBLICATIONS

U.S. Appl. No. 14/868,718, filed Sep. 29, 2015.
(Continued)

*Primary Examiner* — Chelsea E Stinson
*Assistant Examiner* — Mary C Hibbert-Copeland
(74) *Attorney, Agent, or Firm* — Frost Brown Todd LLC

(57) ABSTRACT

A surgical instrument includes a body, a shaft, and an end effector that is operable to compress, staple, and cut tissue. The end effector includes an anvil and a cartridge. The anvil has a curved tip. The curved tip is elastically deformable from a biased curved position when the tip is subject to a force, such as the force exerted on the anvil when tissue is clamped between the anvil and cartridge. The curved and deformable features of anvil provide for an end effector with improved visualization and maneuverability, in particular during procedures involving marching.

20 Claims, 22 Drawing Sheets

(52) U.S. Cl.
CPC ............. *A61B 2017/320044* (2013.01); *A61B 2090/0807* (2016.02)

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,066,166 B2 | 11/2011 | Demmy et al. | |
| 8,136,711 B2 | 3/2012 | Beardsley et al. | |
| 8,210,411 B2 | 7/2012 | Yates et al. | |
| 8,348,123 B2 | 1/2013 | Scirica et al. | |
| 8,371,491 B2 | 2/2013 | Huitema et al. | |
| 8,403,195 B2 | 3/2013 | Beardsley et al. | |
| 8,403,196 B2 | 3/2013 | Beardsley et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,496,153 B2 | 7/2013 | Demmy et al. | |
| 8,573,461 B2 | 11/2013 | Shelton et al. | |
| 8,573,465 B2 | 11/2013 | Shelton | |
| 8,602,288 B2 | 12/2013 | Shelton et al. | |
| 8,616,431 B2 | 12/2013 | Timm et al. | |
| 8,690,039 B2 | 4/2014 | Beardsley et al. | |
| 8,714,429 B2 | 5/2014 | Demmy | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,844,790 B2 | 9/2014 | Demmy et al. | |
| 9,016,546 B2 | 4/2015 | Demmy et al. | |
| 9,039,736 B2 | 5/2015 | Scirica et al. | |
| 9,186,142 B2 | 11/2015 | Fanelli et al. | |
| 9,301,759 B2 | 4/2016 | Spivey et al. | |
| 9,433,416 B2 | 9/2016 | Beardsley et al. | |
| 9,517,065 B2 | 12/2016 | Simms et al. | |
| 9,522,004 B2 | 12/2016 | Demmy | |
| 9,572,574 B2 | 2/2017 | Shelton, IV et al. | |
| 9,597,078 B2 | 3/2017 | Scirica et al. | |
| 9,713,470 B2 | 7/2017 | Scirica et al. | |
| 9,839,420 B2 | 12/2017 | Shelton, IV et al. | |
| 9,936,952 B2 | 4/2018 | Demmy | |
| 9,936,968 B2 | 4/2018 | Demmy et al. | |
| 9,943,311 B2 | 4/2018 | Scirica et al. | |
| 10,080,564 B2 | 9/2018 | Beardsley et al. | |
| D833,010 S | 11/2018 | Harris et al. | |
| 10,166,023 B2 | 1/2019 | Vendely et al. | |
| 10,349,939 B2 | 7/2019 | Shelton, IV et al. | |
| 10,433,863 B2 | 10/2019 | Glutz et al. | |
| 2004/0243151 A1 | 12/2004 | Demmy et al. | |
| 2005/0216055 A1 | 9/2005 | Scirica et al. | |
| 2013/0068818 A1 | 3/2013 | Kasvikis | |
| 2013/0334280 A1 | 12/2013 | Krehel et al. | |
| 2014/0166723 A1 | 6/2014 | Beardsley et al. | |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239041 A1 | 8/2014 | Zerkle | |
| 2014/0239043 A1 | 8/2014 | Simms et al. | |
| 2014/0239044 A1 | 8/2014 | Hoffman | |
| 2015/0173752 A1 | 6/2015 | Demmy et al. | |
| 2015/0272575 A1 | 10/2015 | Leimbach et al. | |
| 2018/0325514 A1 | 11/2018 | Harris et al. | |
| 2018/0325515 A1 | 11/2018 | Harris et al. | |
| 2018/0325516 A1 | 11/2018 | Harris et al. | |
| 2019/0000481 A1 | 1/2019 | Harris et al. | |
| 2019/0076143 A1* | 3/2019 | Smith | A61B 34/30 |
| 2019/0175173 A1 | 6/2019 | Harris et al. | |

FOREIGN PATENT DOCUMENTS

WO  WO 2013/151888 A1  10/2013
WO  WO 2017/083129 A1  5/2017

OTHER PUBLICATIONS

U.S. Appl. No. 15/435,607, filed Feb. 17, 2017.
U.S. Appl. No. 15/435,618, filed Feb. 17, 2017.
U.S. Appl. No. 15/435,631, filed Feb. 17, 2017.
Design U.S. Appl. No. 29/594,332, filed Feb. 17, 2017.
Design U.S. Appl. No. 29/594,340, filed Feb. 17, 2017.
U.S. Appl. No. 16/035,856.
U.S. Appl. No. 16/035,860.
U.S. Appl. No. 16/035,865.
U.S. Appl. No. 16/035,893.
U.S. Appl. No. 16/212,868.
European Search Report, Extended, and Written Opinion dated Aug. 7, 2018 for Application No. EP 18157228.0, 14 pgs.
International Search Report and Written Opinion dated Jun. 27, 2018 for Application No. PCT/US2018/017751, 17 pgs.
U.S. Appl. No. 11/851,495, filed Sep. 7, 2007.
U.S. Appl. No. 16/035,803, filed Jul. 16, 2018.
U.S. Appl. No. 16/035,821, filed Jul. 16, 2018.
U.S. Appl. No. 16/035,825, filed Jul. 16, 2018.
U.S. Appl. No. 16/035,831, filed Jul. 16, 2018.
U.S. Appl. No. 16/035,834, filed Jul. 16, 2018.
U.S. Appl. No. 16/035,872, filed Jul. 16, 2018.
U.S. Appl. No. 60/466,378, filed Apr. 29, 2003.
U.S. Appl. No. 60/843,254, filed Sep. 8, 2006.
European Search Report, Partial, and Written Opinion dated May 4, 2018 for Application No. EP 18157228.0, 18 pages.
European Search Report, Partial, and Written Opinion dated Dec. 9, 2019 for Application No. EP 19186224.2, 11 pgs.
European Search Report, Extended, and Written Opinion dated Dec. 10, 2019 for Application No. EP 19186231.7, 7 pgs.
European Search Report, Partial, and Provisional Written Opinion dated Oct. 31, 2019 for Application No. EP 119186252.3, 16 pgs.
European Search Report, Extended, and Written Opinion dated Jan. 31, 2020 for Application No. EP 119186252.3, 14 pgs.
International Search Report and Written Opinion dated Dec. 6, 2019 for Application No. PCT/IB2019/055980, 13 pgs.
International Search Report and Written Opinion dated Feb. 27, 2020 for Application No. PCT/IB2019/055983, 20 pgs.
Declaration of Non-Establishment of International Search Report and Written Opinion dated Dec. 13, 2019 for Application PCT/IB2019/055984, 6 pgs.

* cited by examiner

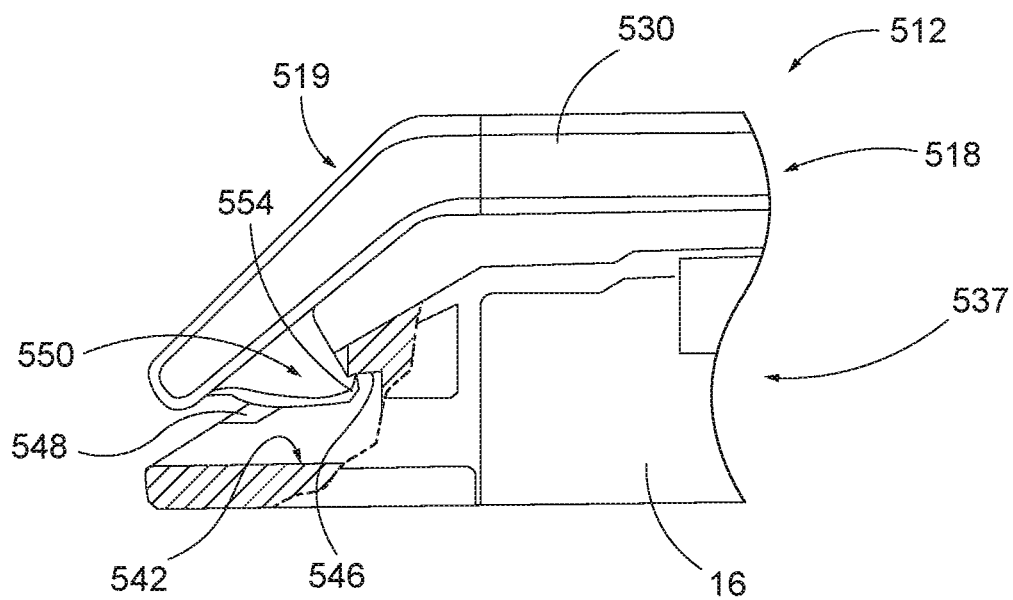
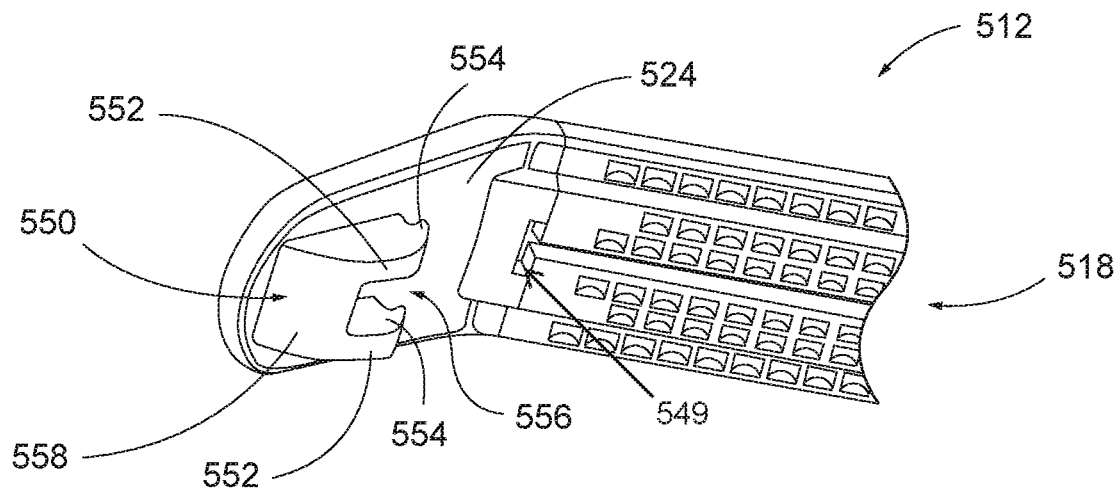
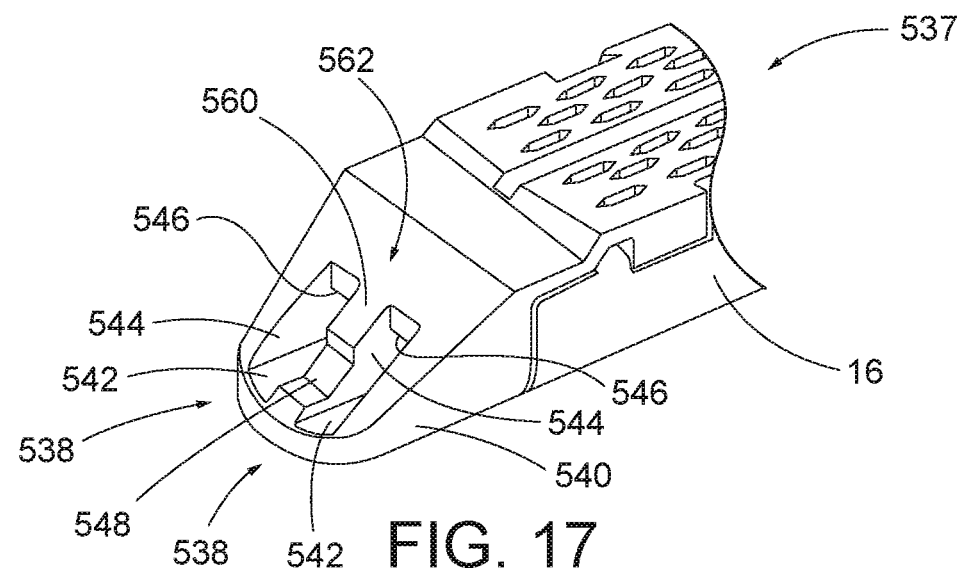
FIG. 16
FIG. 17

SURGICAL STAPLER WITH ELASTICALLY DEFORMABLE TIP

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued as U.S. Pat. No. 8,408,439 on Apr. 2, 2013; and U.S. Pub. No. 2012/0239012, entitled "Motor-Driven Surgical Cutting Instrument with Electric Actuator Directional Control Assembly," published Sep. 20, 2012, issued as U.S. Pat. No. 8,452,914 on Jun. 4, 2013. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 16 depicts an enlarged side view of a distal portion of an exemplary alternative end effector for use with the surgical stapling instruments described herein, shown in partial cross-section to reveal internal features;

FIG. 17 depicts an exploded perspective view of a distal portion of the end effector of FIG. 16;

Figure 1:
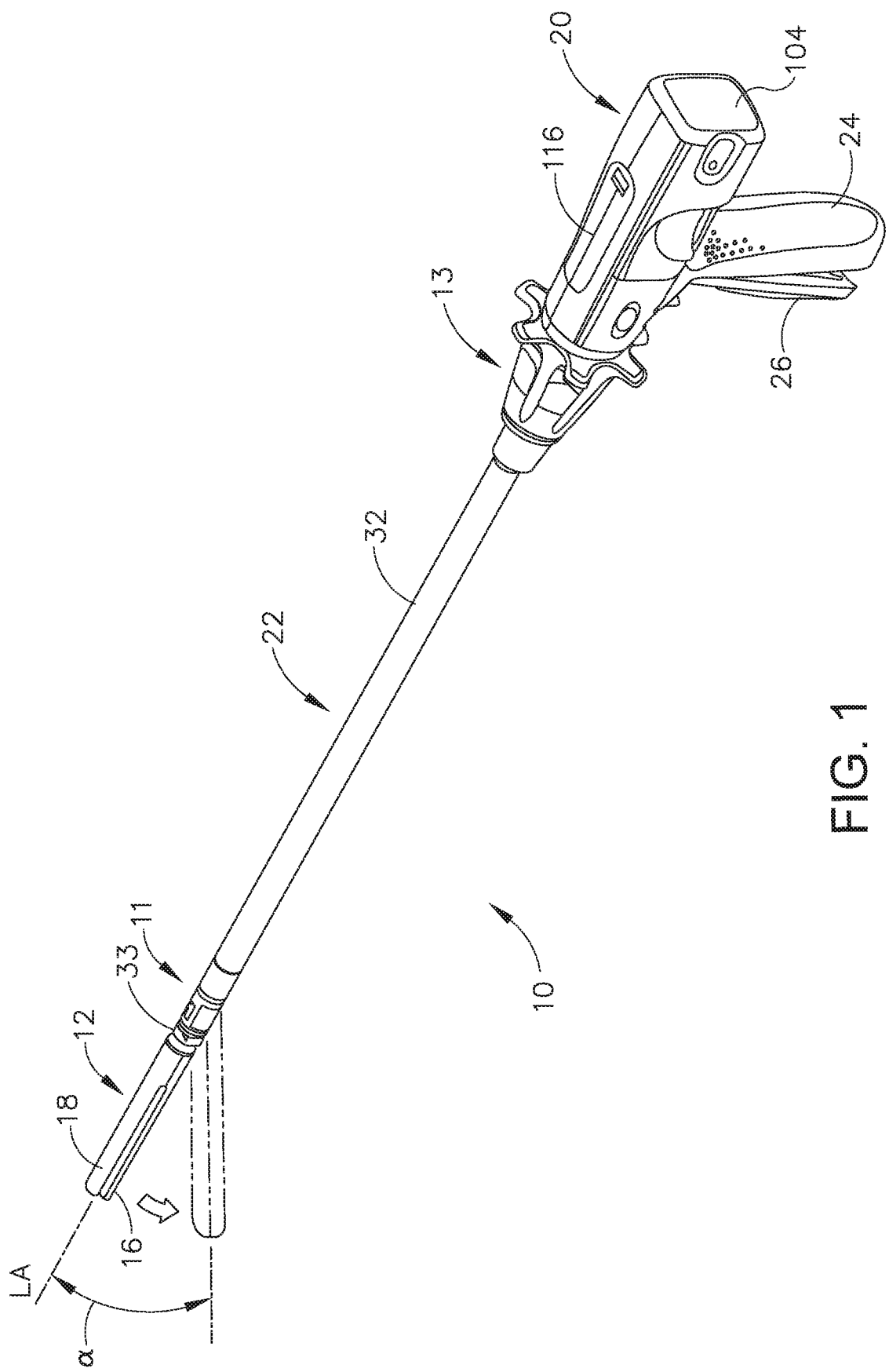
FIG. 1 depicts a perspective view of an exemplary articulating surgical stapling instrument.
Figure 2:
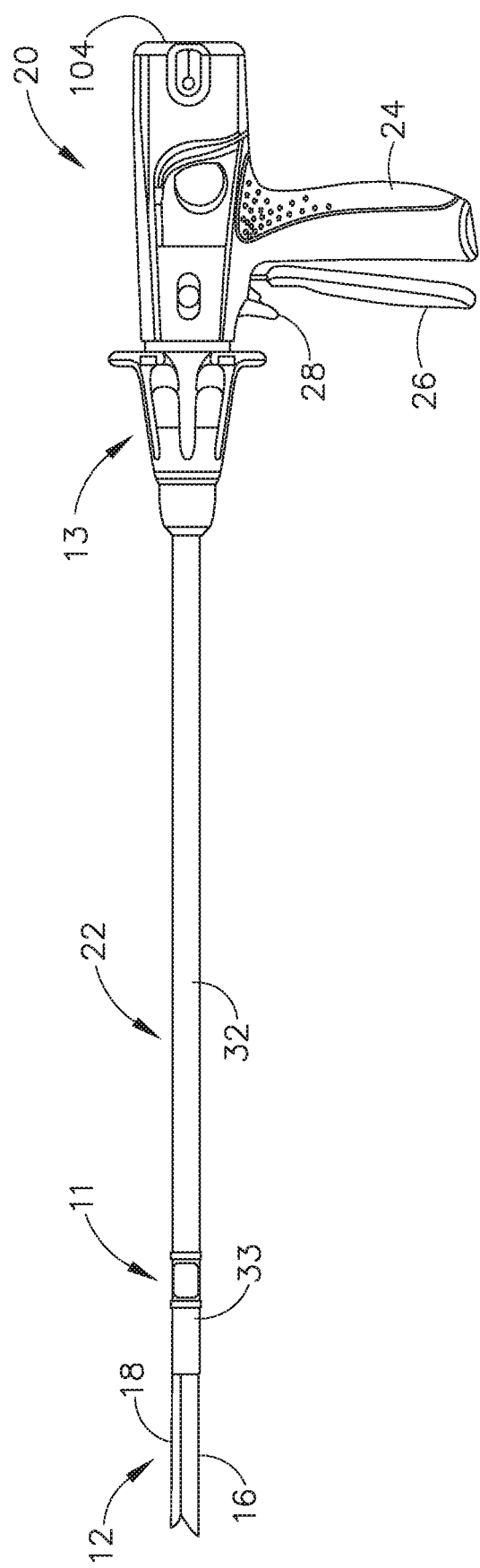
FIG. 2 depicts a side view of the instrument of FIG. 1.

The drawings are not intended to be limiting in any way, and it is contemplated that various embodiments of the invention may be carried out in a variety of other ways, including those not necessarily depicted in the drawings.

The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. EXEMPLARY SURGICAL STAPLER

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector (12) along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. Pat. No. 9,186,142, entitled "Surgical Instrument End Effector Articulation Drive with Pinion and Opposing Racks," issued on Nov. 17, 2015, the disclosure of which is incorporated by reference herein. Articulation joint (11) may also be constructed and operable in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. Pub. No. 2014/0239044, entitled "Installation Features for Surgical Instrument End Effector Cartridge," published on Aug. 28, 2014, issued as U.S. Pat. No. 9,517,065 on Nov. 7, 2017, the disclosure of which is incorporated by reference herein. Anvil (18) may be constructed in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No. 9,517,065 on Dec. 13, 2016, the disclosure of which is incorporated by reference herein; at least some of the teachings of U.S. Pub. No. 2014/0239036, entitled "Jaw Closure Feature for End Effector of Surgical Instrument," published on Aug. 28, 2014, disclosure of which is incorporated by reference herein; and/or at least some of the teachings of U.S. Pub. No. 2014/0239037, entitled "Staple Forming Features for Surgical Stapling Instrument," published on Aug. 28, 2014, issued as U.S. Pat. No. 10,092,292 on Oct. 9, 2018, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. Pub. No. 2014/0239041, entitled "Lockout Feature for Movable Cutting Member of Surgical Instrument," published on Aug. 28, 2014, issued as U.S. Pat. No. 9,717,497 on Aug. 1, 2017, the disclosure of which is incorporated by reference herein. Other suitable forms that firing beam (14) may take will be apparent to those of ordinary skill in the art in view of the teachings herein.

Figure 3:
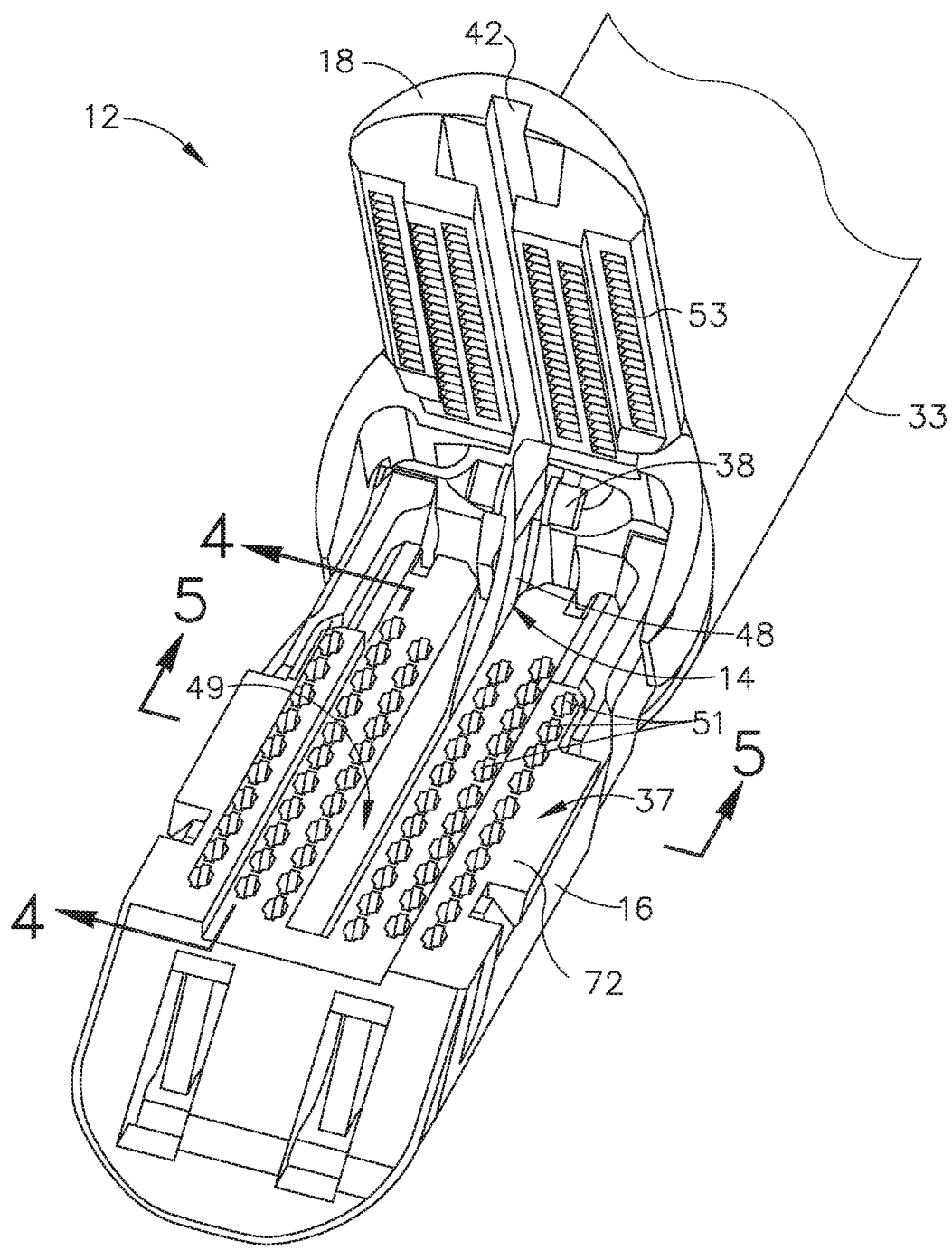
FIG. 3 depicts a perspective view of an opened end effector of the instrument of FIG. 1.
Figure 4A:
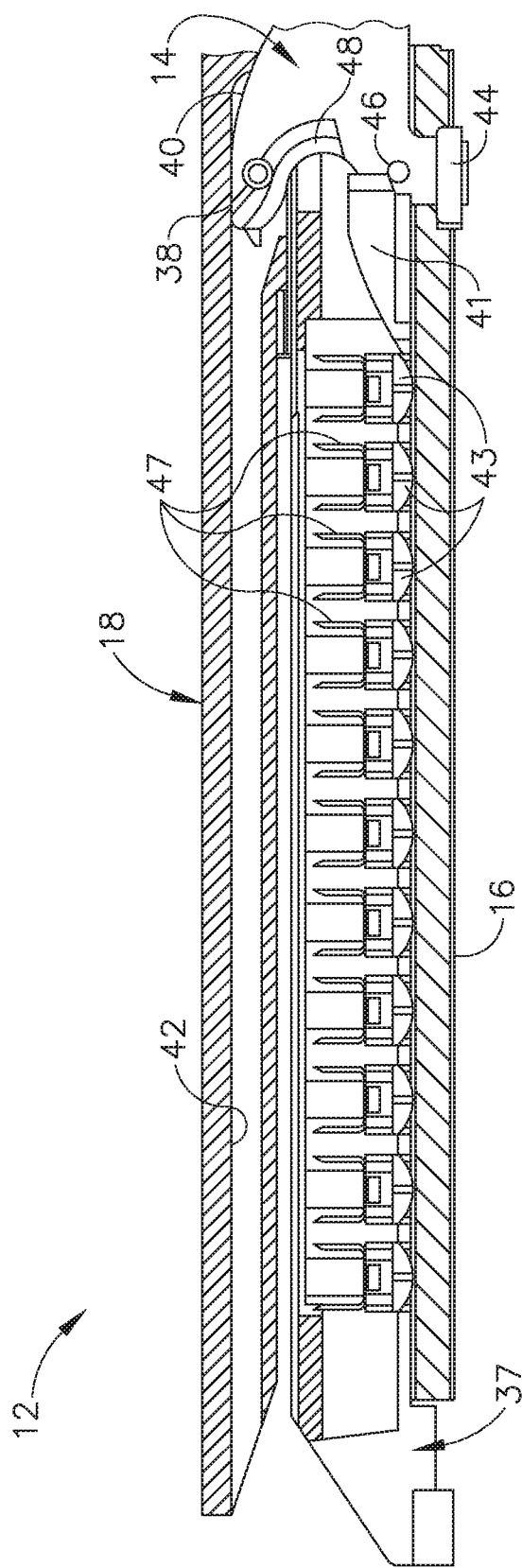
FIG. 4A depicts a side cross-sectional view of the end effector of FIG. 3, taken along line 4-4 of FIG. 3, with the firing beam in a proximal position.
Figure 4B:
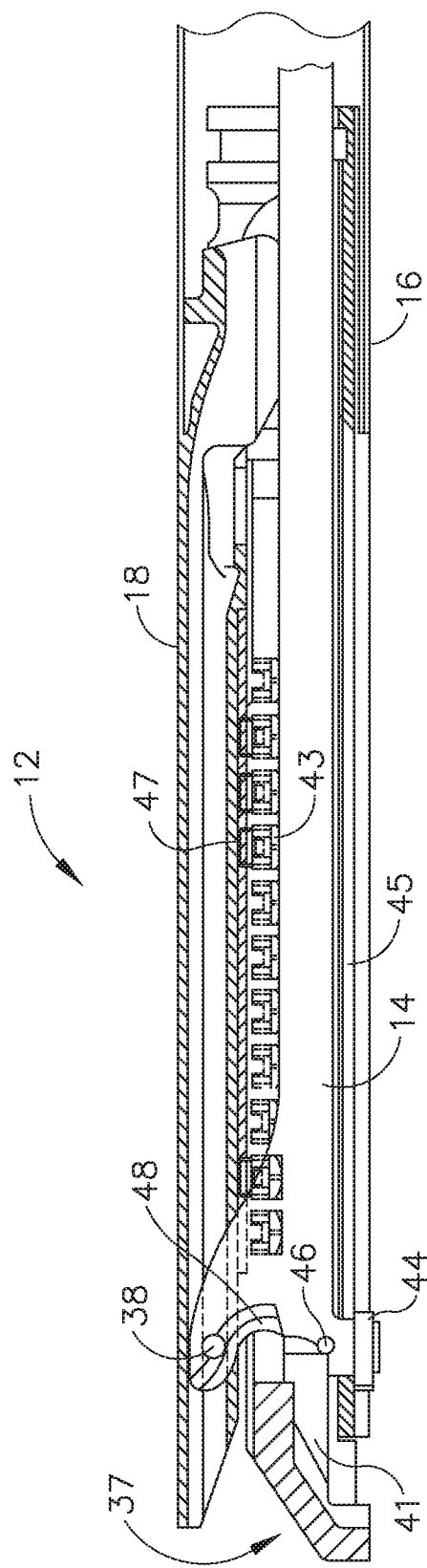
FIG. 4B depicts a side cross-sectional view of the end effector of FIG. 3, taken along line 4-4 of FIG. 3, with the firing beam in a distal position.
Figure 5:
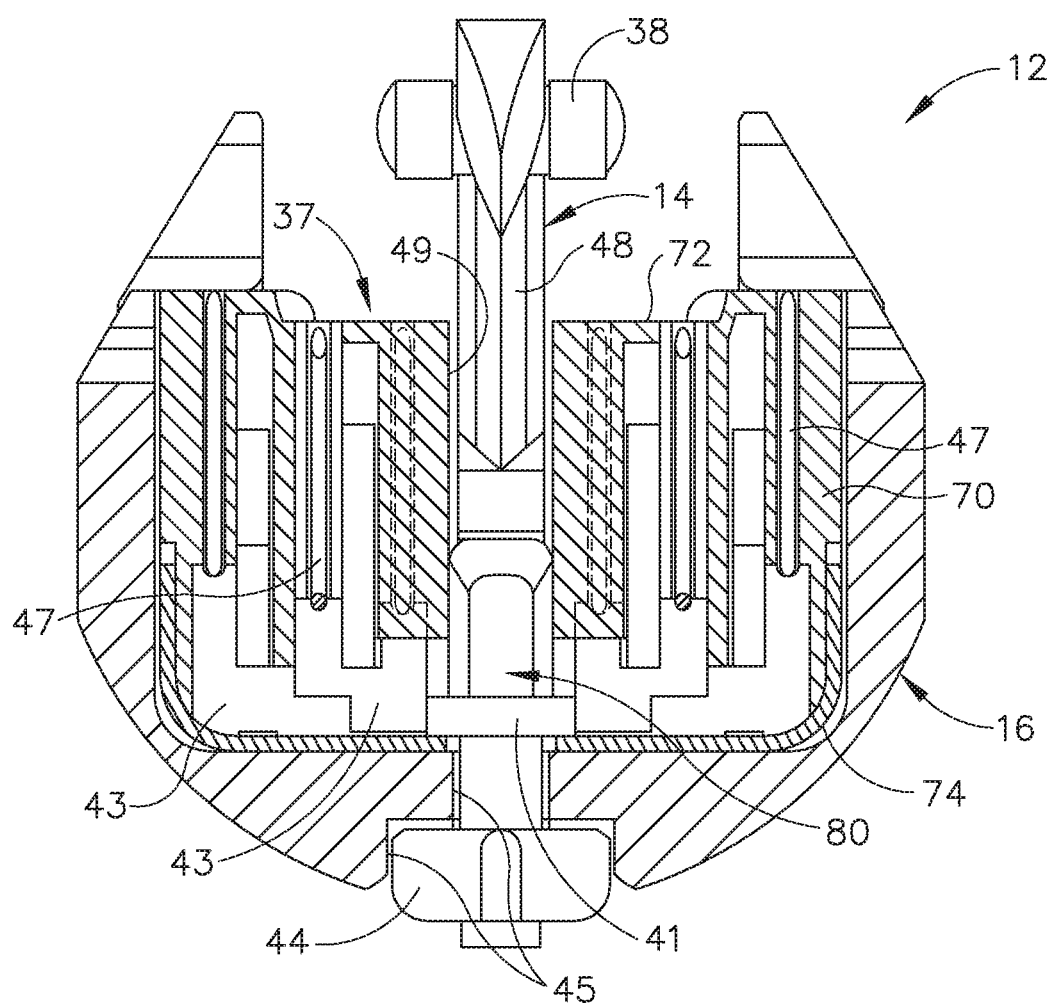
FIG. 5 depicts an end cross-sectional view of the end effector of FIG. 3, taken along line 5-5 of FIG. 3.
Figure 6:
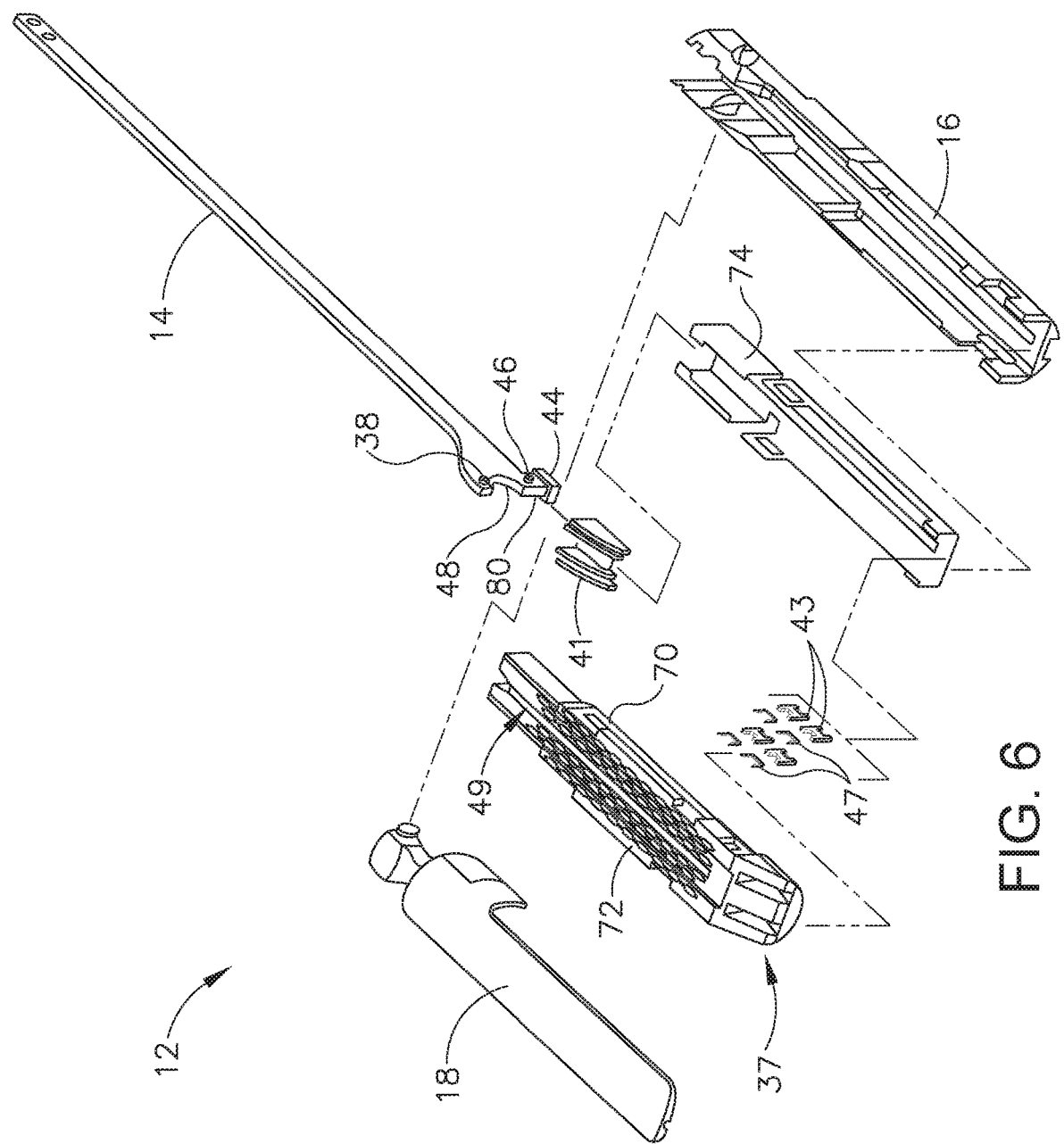
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. Pub. No. 2014/0239042, entitled "Integrated Tissue Positioning and Jaw Alignment Features for Surgical Stapler," published on Aug. 28, 2014, issued as U.S. Pat. No.

9,517,065 on Dec. 13, 2016, the disclosure of which is incorporated by reference herein. In addition or in the alternative, staple cartridge (37) may be constructed and operable in accordance with at least some of the teachings of U.S. Pub. No. 2014/0239044, entitled "Installation Features for Surgical Instrument End Effector Cartridge," published on Aug. 28, 2014, issued as U.S. Pat. No. 9,808,248 on Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
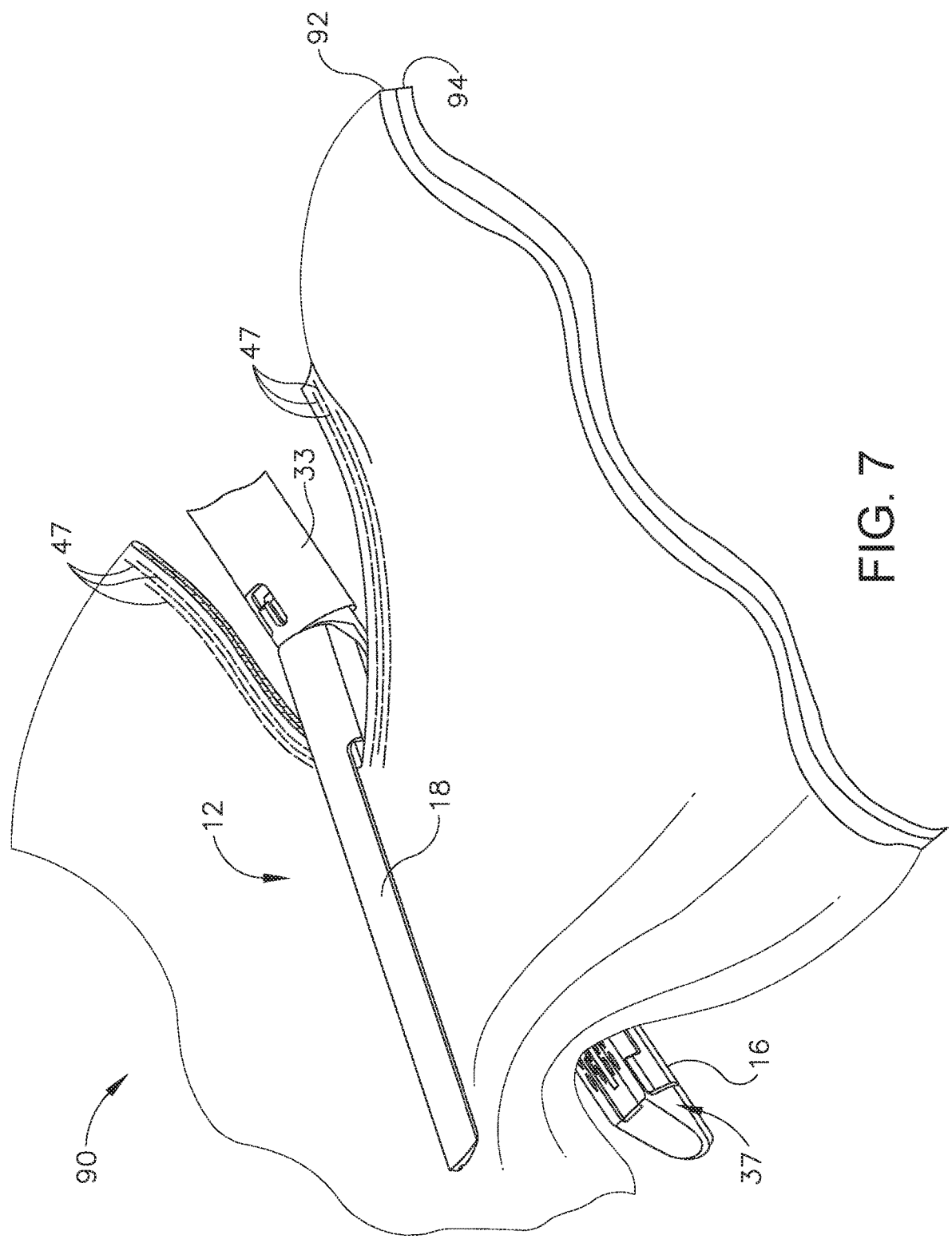
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

In one version, instrument (10) provides motorized control of firing beam (14). Exemplary components that may be used to provide motorized control of firing beam (14) are shown and described in US. Pub. No. 2014/0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein. In addition to or in lieu of the foregoing, at least part of the motorized control may be configured in accordance with at least some of the teachings of U.S. Pat. No. 8,210,411, entitled "Motor-Driven Surgical Instrument," issued Jul. 3, 2012, the disclosure of which is incorporated by reference herein. In addition to or in lieu of the foregoing, the features operable to drive firing beam (14) may be configured in accordance with at least some of the teachings of U.S. Pub. No. 2012/0239012, issued as U.S. Pat. No. 8,453,914 on Jun. 4, 2013, the disclosure of which is incorporated by reference herein; and/or in accordance with at least some of the teachings of U.S. Pub. No. 2012/0239012, issued as U.S. Pat. No. 8,453,914 on Jun. 4, 2013, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

Instrument (10) may also include a lockout switch and lockout indicator as shown and described in US. Pub. No. 2014/0239043, entitled "Distal Tip Features for End Effector of Surgical Instrument," published on Aug. 28, 2014, issued as U.S Pat. No. 9,622,746 on Apr. 18, 2017, the disclosure of which is incorporated by reference herein. Additionally, a lockout switch and/or lockout indication and associated components/functionality may be configured in accordance with at least some of the teachings of U.S. Pat. No. 7,644, 848, entitled "Electronic Lockouts and Surgical Instrument Including Same," issued Jan. 12, 2010, the disclosure of which is incorporated by reference herein.

Instrument (10) also include a manual return switch (116) configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide further functionality in accordance with at least some of the teachings of U.S. Pub. No. 2014/

0239043, entitled "Distal Tip Features for End Effector of Surgical Instrument," published on Aug. 28, 2014, issued as U.S. Pat. No. 9,622,746 on Apr. 18, 2017, the disclosure of which is incorporated by reference herein.

In describing the operation of instrument (10), use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

It should be understood that instrument (10) may be configured and operable in accordance with any of the teachings of U.S. Pat. Nos. 4,805,823; 5,415,334; 5,465,895; 5,597,107; 5,632,432; 5,673,840; 5,704,534; 5,814,055; 6,978,921; 7,000,818; 7,143,923; 7,303,108; 7,367,485; 7,380,695; 7,380,696; 7,404,508; 7,434,715; 7,721,930; U.S. Pub. No. 2010/0264193; issued as U.S. Pat. No. 8,408,439 on Apr. 2, 2013; and/or 2012/0239012, issued as U.S. Pat. No. 8,453,914 on Jun. 4, 2013. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. EXEMPLARY END EFFECTOR WITH VISUALIZATION, LEAD-IN, AND GATHERING FEATURE

In some instances, it may be desirable to provide the user with better visualization of end effector (12). In particular, as end effector (12) is inserted into a surgical site, the user may rotate shaft (22) of instrument (10) during the procedure. As a result, end effector (12) also rotates. As end effector (12) rotates, it may be desirable for the user to have visual access to the surgical site. For instance, the user may wish to see the interface or contact between tissue (90) and end effector (12). Since end effector (12) may be rotated about the longitudinal axis (LA) relative to handle portion (20), the user may view the surgical site such that lower jaw (16) of end effector is visible rather than anvil (18). Alternatively, end effector (12) could be rotated such that when the user views end effector (12), anvil (18) is visible by the user. It may be desirable to provide visibility of the surgical site for the user beyond what is possible in instrument (10) of FIG. 1. For instance, in the case of some surgical procedures where fluid carrying vessels are transected and stapled, it may be desirable to have visual confirmation that anvil (18) and lower jaw (16) completely cover the vessel to be cut, such that the vessel may be fully cut and stapled in one single actuation. In other words, the user may wish to avoid cutting and stapling only a portion of a vessel. Thus, some means of visual monitoring and/or feedback may be desirable so that the user will know that end effector (12) has been positioned properly within the surgical site for anvil (18) and lower jaw (16) to fully clamp the vessel. One potential way of monitoring the surgical site may include improving visualization of the area adjacent to the distal tip of lower jaw (16) and anvil (18). Furthermore, not only visualization of the distal end of end effector (12) may be desirable, but also it may be desirable to construct end effector (12) such that the distal end of anvil (18) is configured to urge tissue (e.g., a large vessel) proximally into the space between anvil (18) and lower jaw (16) as anvil (18) closes toward lower jaw (16).

Figure 8:
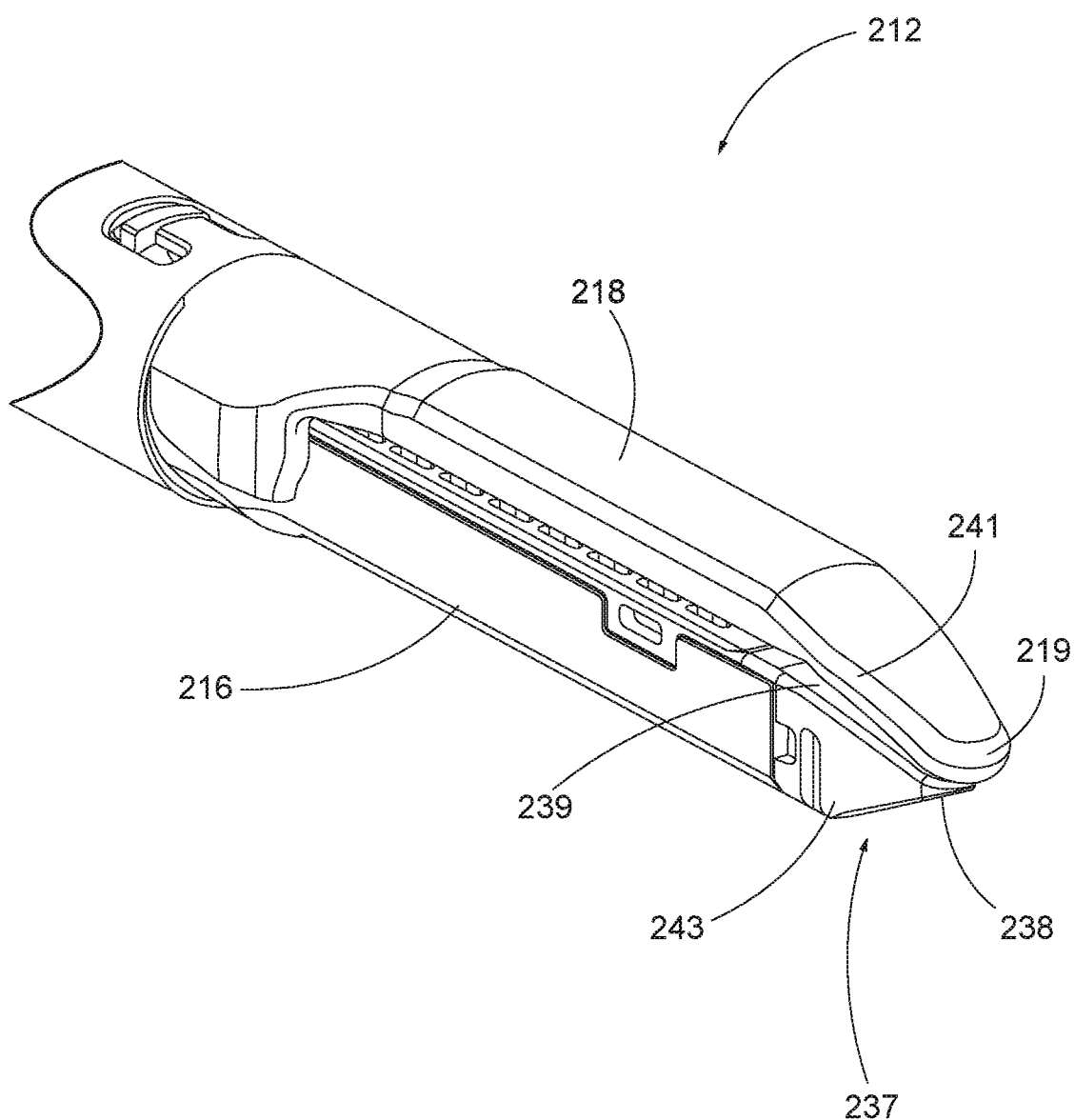
FIG. 8 depicts a perspective view of an alternative version of an end effector with an angled anvil and an angled cartridge.

FIG. 8 depicts an exemplary end effector (212) comprising an anvil (218) and a lower jaw (216). It will be appreciated that end effector (212) may be used in place of end effector (12) of instrument (10). End effector (212) may be integrally formed with instrument (10) or in the alternative may be interchangeable with end effector (12) of instrument (10).

Anvil (218) is operable to pivot relative to lower jaw (216). Anvil (218) and lower jaw (216) may clamp tissue (90) similarly to clamping performed by anvil (18) and lower jaw (16) shown in FIG. 1. End effector (212) further comprises a cartridge (237) operable to be placed in lower jaw (216) similarly to cartridge (37) shown in FIG. 3.

Figure 9:
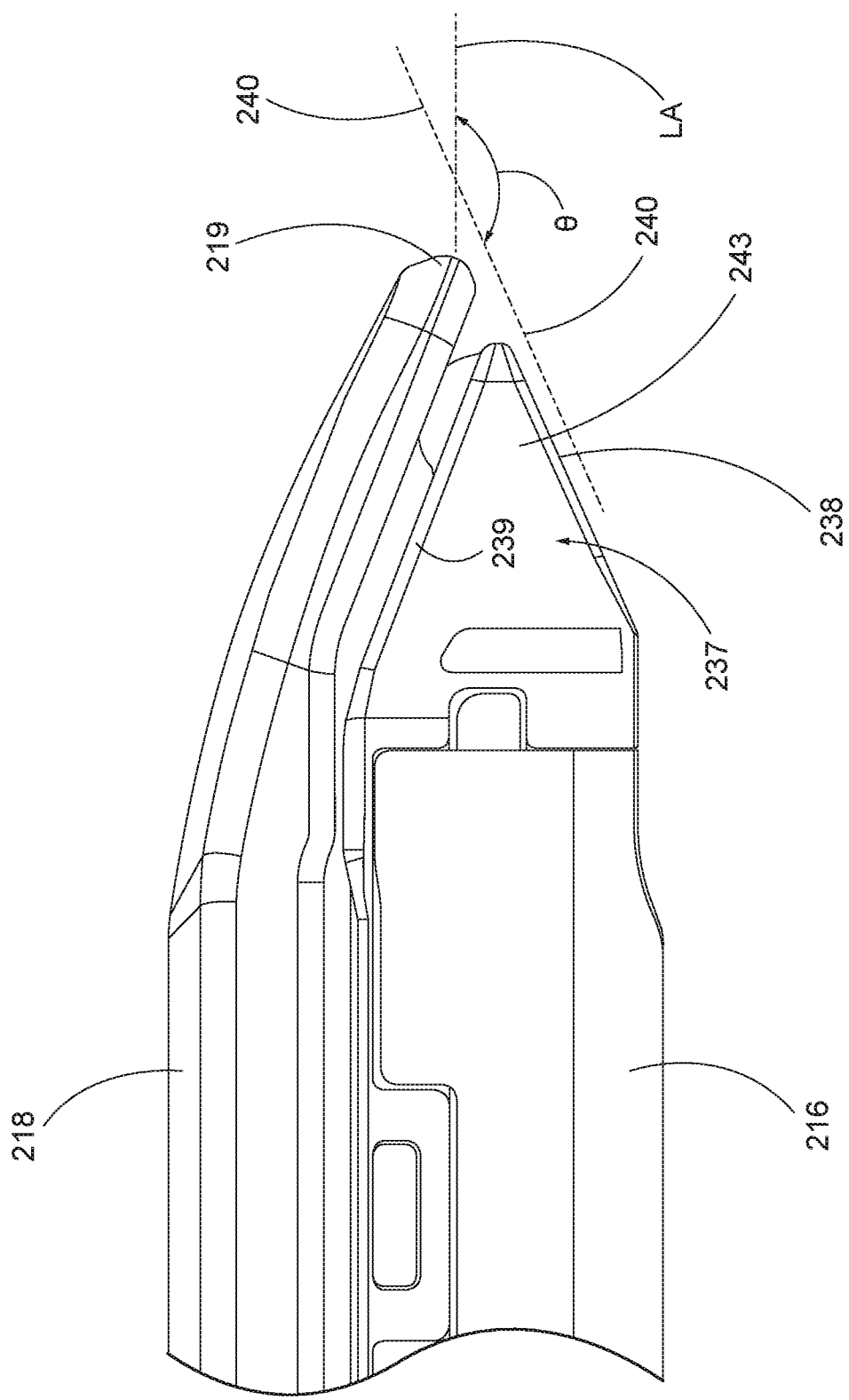
FIG. 9 depicts an enlarged, side view of the end effector of FIG. 8.
Figure 10:
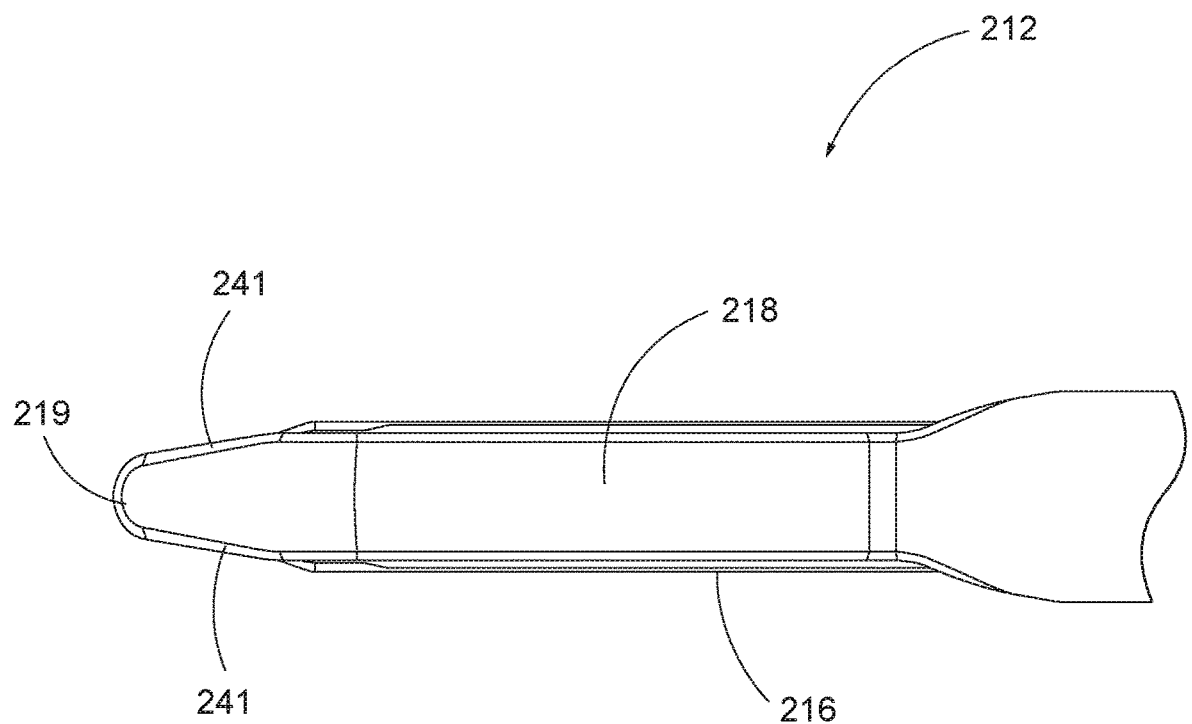
FIG. 10 depicts an enlarged top view of the end effector of FIG. 8.

Anvil (218) as can be seen in FIGS. 8-10 has an elongated shape where the distal portion of anvil (218) angles toward cartridge (237). The distal portion of anvil (218) angles toward cartridge (237) such that the distal most tip (219) of anvil (218) extends distally longitudinally further than cartridge (237). Though in some versions, distal tip (219) may extend to a distance longitudinally equal to cartridge (237) or proximal relative to the distal most point on cartridge (237). Furthermore, anvil (218) angles toward cartridge (237) through a gentle slope. As seen best in FIG. 10, anvil (218) includes sides (241) that taper as they approach the distal most tip (219) of anvil (218). By way of example, anvil (218) is shaped in FIG. 8 similarly to an inverted ski tip. The angled shape of anvil (218) may provide easier insertion of end effector (212) into a surgical site. For instance, the gentle slope or inverted ski tip shape of anvil (218) may provide an atraumatic tissue deflection surface as anvil (218) contacts or moves through tissue. Such atraumatic tissue deflection may include urging tissue (e.g., a large vessel) proximally into the space between anvil (218) and lower jaw (216) as anvil (218) closes toward lower jaw (216). Once placed into a surgical site, the angled shape of anvil (218) may also provide better maneuverability of end effector (212) and better visibility of the distal end of end effector (212) in relation to anatomical structures at the surgical site. Other suitable variations of anvil (218) will be apparent to one of ordinary skill in the art in view of the teachings herein.

Cartridge (237) is operable to hold staples similar to staples (47) shown in FIG. 4A for driving into tissue. As shown in FIG. 9, the distal end of cartridge (237) has a triangular profile. In particular, the distal end of cartridge (237) comprises an upper tapered surface (239) and a lower tapered surface (238). Additionally, the distal end of cartridge (237) comprises a tapered side surface (243) on each side. In the present example, each tapered side surface (243) of cartridge (237) generally aligns with the taper presented by sides (241) of anvil (218). Thus, as shown in FIG. 10, side surfaces (243) of cartridge (237) do not extend outwardly from longitudinal axis (LA) of end effector (212) past sides (241) of anvil (218). Upper tapered surface (239) and lower tapered surface (238) lead to the distal most end of cartridge (237). Lower tapered surface (238) defines a sight line (240) such that once end effector (212) is inserted into a surgical site, the user can see along sight line (240). Sight line (240) extends along the edge of lower tapered surface (238). It will be appreciated that the planar shape of lower tapered surface (238) may be operable to allow the user to visualize and/or nearly visualize the distal tip (219) of anvil (218). In particular, sight line (240) intersects longitudinal axis (LA), which extends longitudinally through end effector (212), to form a viewing angle (θ).

Viewing angle (θ) may establish the relative visibility that a user has regarding distal tip (219). In particular, the user can see in front of distal tip (219) along any line of sight that passes through the intersection of sight line (240) and longitudinal axis (LA) within viewing angle (θ). For instance, as viewing angle (θ) increases, the user would have greater visibility of the area immediately in front of distal tip (219) from proximal vantage points; whereas as viewing angle (θ) decreases, the user has less visibility of the area in front of distal tip (219) from proximal vantage points. In al some versions, viewing angle (θ) defines an angle greater than 90 degrees. Additionally, in some versions, viewing angle (θ) defines an angle greater than 135 degrees. Other suitable angles for viewing angle (θ) will be apparent to one of ordinary skill in the art in view of the teachings herein. In the illustrated version, the user generally looks along sight line (240) or along some other line of sight within viewing angle (θ), thus, the user has visibility along sight line as well as any area within viewing angle (θ). The underside of distal tip (219) is further slightly rounded to aid in the visibility of the intersection of longitudinal axis (LA) and sight line (240).

When tissue (90) is clamped between a closed cartridge (237) and anvil (218), the user can look along sight line (240) or elsewhere within viewing angle (θ) to see, for instance, precisely where anvil (218) has clamped tissue (90). Furthermore, the user would be able to determine whether the tissue is completely clamped between anvil (218) and cartridge (237) such that tissue does not spill over the end of end effector (212). The user may be able to also visualize the quality of the clamp between anvil (218) and cartridge (237) against tissue (90). It will be appreciated that in some instances, end effector (212) may be rotated before, during, or after clamping tissue (90). As a result, the tapered shape of anvil (218) may also provide more accessible viewing of distal tip (219) or substantially adjacent distal tip (219). The taper of anvil (218) along with lower tapered surface (238) of cartridge (237) may further promote easy insertion of end effector (212) into tissue in an atraumatic manner. Furthermore, it may be easier to fit end effector (212) through a trocar or other devices operable to introduce end effector (212) into a surgical site due to the tapered end of end effector (212). For instance, once distal tip (219) is fit into a trocar, lower tapered surface (238) and the tapered shape of anvil (218) may provide a lead-in, guiding the rest of end effector (212) into the trocar. In view of the teachings herein, those of ordinary skill in the art will further appreciate that visibility and maneuverability can be enhanced by the tapered design for both sides (241) of anvil (218) and each side (243) of cartridge (237).

In addition to the foregoing, end effector (212) and versions of instrument (10) incorporating end effector (212) may be configured and operable in accordance with at least some of the teachings of U.S. Pat. No. 9,186,142, entitled "Surgical Instrument End Effector Articulation Drive with Pinion and Opposing Racks," issued Nov. 17, 2015, the disclosure of which is incorporated by reference herein; U.S. Pub. No. 2014/0239041, entitled "Lockout Feature for Movable Cutting Member of Surgical Instrument," published Aug. 28, 2014, issued as U.S. Pat. No. 9,717,497 on Aug. 1, 2017, the disclosure of which is incorporated by reference herein; U.S. Pat. No. 9,517,065, entitled "Integrated Tissue Positioning and Jaw Alignment Features for Surgical Stapler," issued Dec. 13, 2016, the disclosure of which is incorporated by reference herein; U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; U.S. Pub. No. 2014/0239043, entitled "Distal Tip Features for End Effector of Surgical Instrument," published Aug. 28, 2014, issued as U.S. Pat. No. 9,622,746 on Apr. 18, 2017, the disclosure of which is incorporated by reference herein; U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein; U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein; and/or U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Further modifications that may be incorporated into end effector (212) will be described in greater detail below.

III. END EFFECTORS WITH CURVED ELASTICALLY DEFORMABLE ANVIL TIPS

In some procedures, it may be necessary to cut along tissue or through tissue where more than one cutting sequence is necessary to complete the procedure—in other words making sequential cuts along a continuous path. In such procedures, this sequential cutting technique can be defined as "marching." With procedures that involve marching, instrument (10) may be placed at the surgical site, actuated to cut and staple, then removed from the surgical site for installing a new cartridge (37), and then be placed back at the surgical site again for the next cut and staple along the same path in which the previous cutting and stapling cycle occurred. This process is repeated until the cut and staple procedure is complete. As can be seen in FIGS. 4A-4B and FIG. 7, the distal end configuration of end effector (12) provides a gap between the distal end of anvil (18) and the distal end of cartridge (37). This gap may facilitate marching by providing an atraumatic space for tissue to enter the distal end of end effector (12) at the beginning of each marching step.

As noted above, the distal end configuration of end effector (212) is different from the distal end configuration of end effector (12); with the different configuration of end effector (212) providing different potential advantages. In particular, the distal end configuration of end effector (212) may provide improved maneuverability and improved visibility of the relationship between the distal end of end effector (212) and adjacent anatomical structures. In addition, the distal end configuration of end effector (212) may provide tissue-gathering effects by urging tissue proximally into the space between anvil (218) and lower jaw (216) as anvil (218) is closed toward lower jaw (216). However, in versions where all the structures of end effector (212) are rigid, the bent configuration of distal tip (219) of anvil (218) may not lend itself well to marching operations, as distal tip (219) may impart trauma to tissue that is not gathered into the space between anvil (218) and lower jaw (216) as anvil (218) is closed toward lower jaw (216). Thus, in versions where all the structures of end effector (212) are rigid, end effector (212) may be best suited for cutting and stapling operations (e.g., vessel transection) where all of the tissue that is to be cut and stapled is gathered proximal to distal tip (219).

In view of the foregoing, it may be desirable to provide a variation of end effectors (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). The following describes several merely illustrative examples of such variations of end effectors (12, 212). In the following examples, an anvil has a distal tip that is resiliently biased to assume a bent or angled configuration like distal tip (219); yet the resiliently biased distal tip is deflectable away from the lower jaw in response to a sufficient load on the distal tip. It will be understood in view of the teachings herein that providing an anvil with an elastically deformable angled distal tip portion can provide an additional level of maneuverability benefits in terms of navigating through tissue to a surgical site. In this manner, the deformable distal tip portion may deflect or deform to promote smooth and atraumatic movement of the end effector through tissue, particularly during marching operations. Additionally, with an anvil having a bias to an angled position when not in a loaded state or contacted by surrounding tissue, enhanced visualization during tissue capture and cutting can be achieved compared to using end effectors with a straight or non-angled anvil. Moreover, an anvil with a distal tip that is biased to an angled position may provide some degree of tissue gathering effects up until reaching a load point that would be associated with marching rather than being associated with simply gathering a relatively small tissue structure between the anvil and lower jaw.

Figure 11:
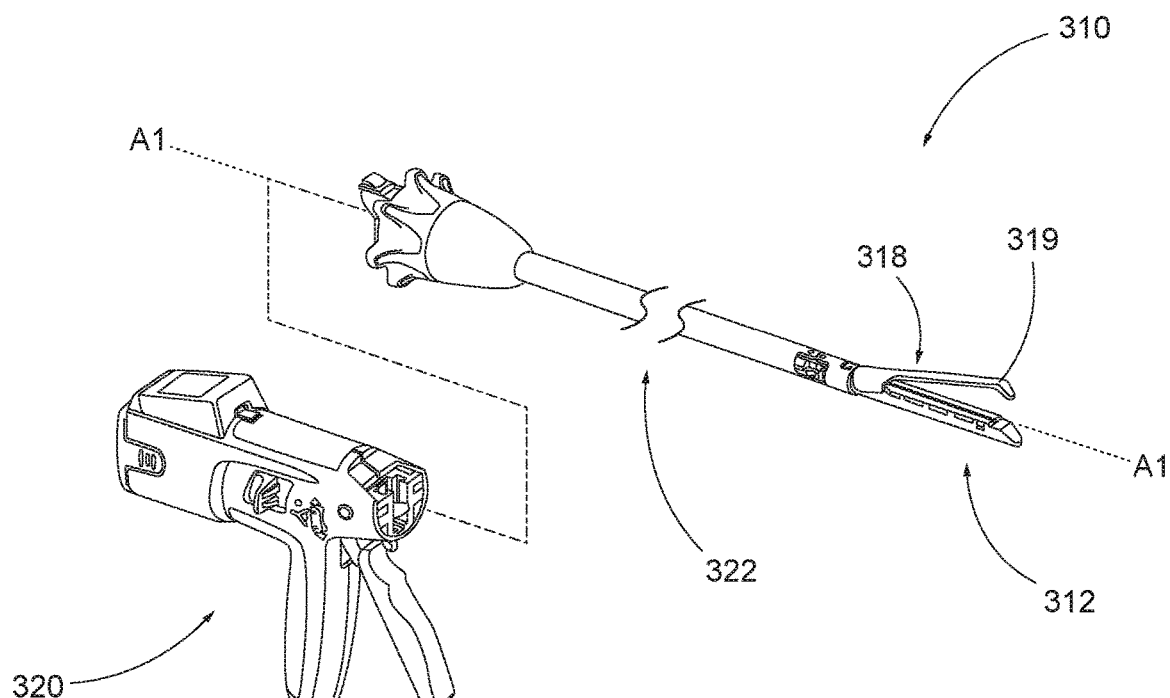
FIG. 11 depicts a perspective view of an exemplary surgical stapling instrument having an end effector with a curved elastically deformable tip section.

FIG. 11 shows another exemplary instrument (310) configured as a surgical stapler. Instrument (310) comprises a handle portion (320) and a shaft (322). Instrument (310) has a modular configuration such that shaft (322) is selectively removable from, and attachable to, handle portion (320). Instrument (310) is configured similarly to instrument (10) such that the operability and use of instrument (310) is the same as described above for instrument (10) with the added feature of instrument (310) being a modular configuration. With its modular configuration, instrument (310) provides a way to change the end effector. Such a change in the end effector may be made to replace an otherwise worn end effector, or to provide for a different end effector configuration based on the procedure or user preference. In addition to or in lieu of the foregoing, features operable for providing the modular configuration of instrument (310) may be configured in accordance with at least some of the teachings of U.S. patent application Ser. No. 14/868,718, entitled "Surgical Stapling Instrument with Shaft Release, Powered Firing, and Powered Articulation," filed Sep. 29, 2015, issued as U.S. Pat. No. 10,182,813 on Jan. 22, 2019, the disclosure of which is incorporated by reference herein. Other suitable components, features, and configurations for providing instrument (310) with a modular configuration will be apparent to those of ordinary skill in the art in view of the teachings herein. Moreover, it will be understood by those of ordinary skill in the art in view of the teachings herein, that instrument (10) may be modified to incorporate a modular configuration as shown and described with respect to instrument (310) or other instruments incorporated by reference herein.

In the illustrated example of FIG. 11, instrument (310) comprises an end effector (312) having an anvil (318) that has an angled distal tip (319). Furthermore, distal tip (319) of anvil (318) is elastically deformable. In this manner, and as shown best in FIGS. 12A and 12B, angled distal tip (319) is operable to elastically deform from a first angled position to a second position. The second position for angled distal tip (319) may be substantially straight in some versions, but may be angled to a degree (e.g., slightly above or slightly below the longitudinal axis (A1)) in other versions. It should be understood that the second position for angled distal tip (319) may be defined by the characteristics (e.g., thickness, density, etc.) of the tissue that is being captured between anvil (318) and lower jaw (16). In the present example, end effector (312) is provided on shaft (322) that is detachable from handle portion (320). By way of example only, shaft (322) may be detachable from handle portion (320) in accordance with at least some of the teachings of U.S. Pub. No. 2015/0272575, entitled "Surgical Instrument Comprising a Sensor System," published Oct. 1, 2015, issued as U.S. Pat. No. 9,919,642 on Mar. 13, 2018, the disclosure of which is incorporated by reference herein. In some other versions, shaft (322) is not detachable from handle portion (320).

It will be appreciated that end effector (312) may be used in place of end effector (12) shown in FIG. 1. In some versions, end effector (312) may be integrally formed with shaft (22) or alternatively may be separately formed and then combined. In some versions, end effector (312) may be provided for use in robotic systems. In such robotic systems, modular shaft (322) having end effector (312) may be attachable to a portion of the robotic system for use such that handle portion (320) is replaced by components of the robotic system. Still in other examples, end effector (312) may be adapted for use with a robotic system in a manner where end effector (312) connects with the robotic system without necessarily connecting the entire modular shaft (322). In view of the teachings herein, other ways to incorporate an end effector having an angled elastically deformable anvil tip into a user operated or robotic operated instrument will be apparent to those of ordinary skill in the art.

Figure 12A:
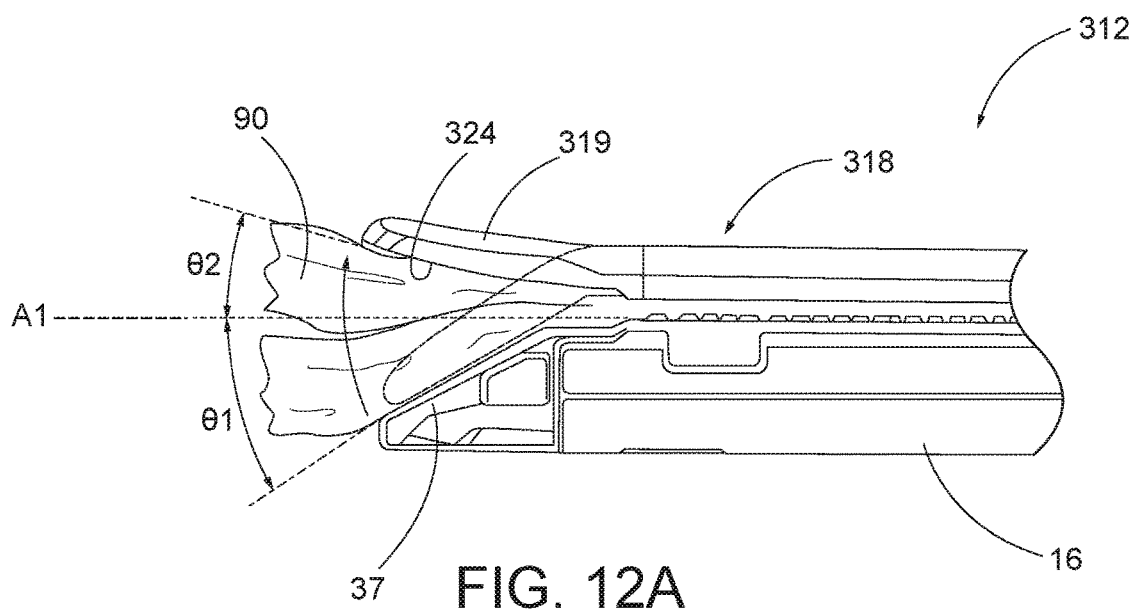
FIG. 12A depicts an enlarged side view of a distal portion of the end effector of FIG. 11.

FIG. 12A shows an enlarged side view of the distal end of end effector (312). End effector (312) comprises anvil (318) and lower jaw (16) that accepts cartridge (37) as described above with respect to instrument (10). Anvil (318) pivotably rotates toward lower jaw (16) in the same manner as anvil (18) as described above with respect to instrument (10). In this configuration, end effector (312) is similar to end effector (12), however, anvil (318) comprises angled distal tip (319) that is elastically deformable. As shown in FIG. 12A, tip (319) is imparted with a bias to an angled position that is shown in FIG. 11 and in phantom in FIG. 12A. Tip (319) assumes this angled position when end effector (312) is not clamping tissue and is open, as shown in FIG. 11; or closed without clamping tissue, as shown in phantom in FIG. 12A. In instances when end effector (312) is in this angled state or position, end effector (312) can be considered not loaded or in a non-loaded state or position. Conversely when end effector (312) is clamping tissue, end effector (312) can be considered loaded or in a loaded state or position.

When closed and not clamping tissue between anvil (318) and lower jaw (16), tip (319) contacts cartridge (37). In this position, an underside surface (324) of tip (319) defines a plane that intersects a longitudinal axis (A1) defined by shaft (322) to form an angle (θ1). When closed and clamping tissue (90) between anvil (318) and lower jaw (16), underside surface (324) of tip (319) contacts tissue (90). In this position, underside surface (324) of tip (319) defines a plane that intersects longitudinal axis (A1) to form an angle (θ2). In the illustrated example of FIG. 12A, angles (θ1, θ2) are relative to longitudinal axis (A1), and the sum of angles (θ1, θ2) represent the range of motion distal tip (319) undergoes. By way of example only, and not limitation, in some examples angle (θ1) is between about 20 and about 70 degrees, or more particularly between about 30 degrees and about 50 degrees, in a downward direction from longitudinal axis (A1) toward cartridge (37). By way of example only, and not limitation, in some examples angle (θ2) is between about 0 and about 90 degrees in an upward direction from longitudinal axis (A1) away from cartridge (37). By way of example only, and not limitation, in some examples the range of motion undergone by tip (319) is between about 20 degrees and about 110 degrees. The angles described for angles (θ1, θ2) are exemplary only and not limiting. Other suitable angles will be apparent to those of ordinary skill in the art in view of the teachings herein.

Additionally, in some instances longitudinal axis (A1) represents a zero-degree reference and angles relative thereto may be positive or negative. For instance, where an angle is in a downward direction from longitudinal axis (A1) toward cartridge (37), the angle may be characterized as a negative angle. Similarly, where an angle is in an upward direction from longitudinal axis (A1) away from cartridge (37), the angle may be characterized as a positive angle. When using these conventions, the range of motion of distal tip (319) due to deformation can be understood as the sum of the absolute value of the angle when distal tip (319) is in the position contacting cartridge (37), and the angle when distal tip (319) is in the deformed state when clamping tissue.

Figure 12B:
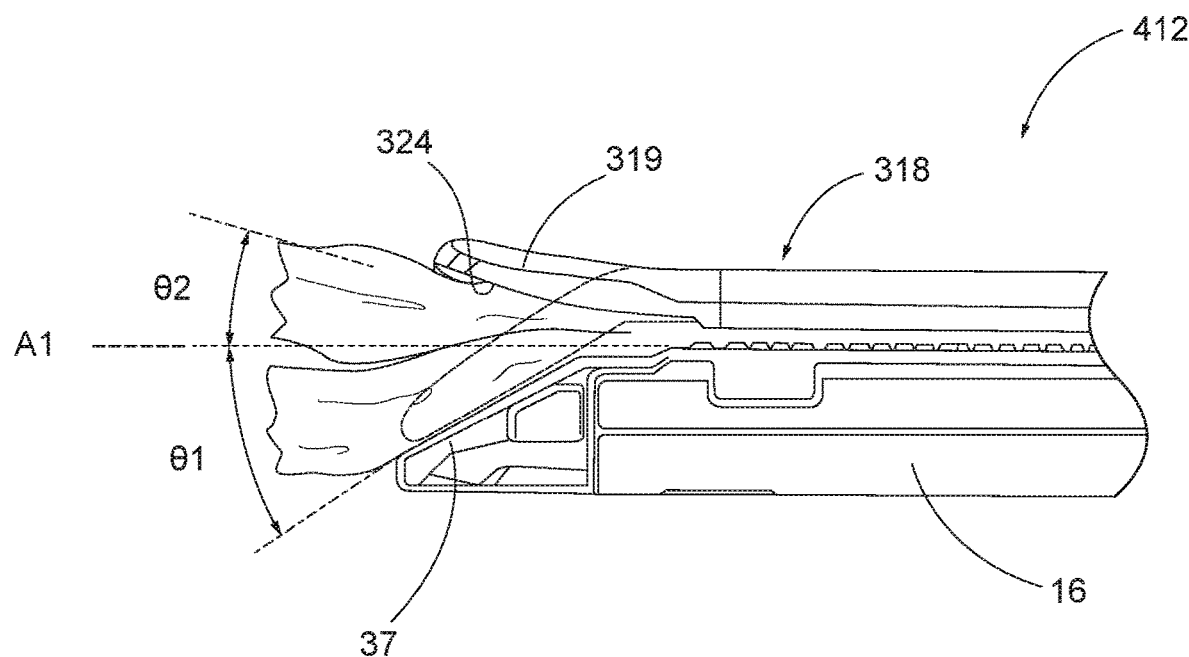
FIG. 12B depicts an enlarged side view of a distal portion of an alternate end effector similar to that of FIG. 11.

FIG. 12B shows another side view of an alternate end effector (412) similar to end effector (312) of FIG. 12A. With end effector (312), when anvil (318) is in its angled and non-deformed state (as seen in phantom in the view of FIG. 12A), anvil (318) extends to a point even with or proximal to the distal most end of cartridge (37). When anvil (318) is deformed such that it is deflected upwardly, the end of distal tip (319) extends to a point just distal to the distal most end of cartridge (37). With end effector (412), as shown in FIG. 12B, when anvil (318) is in its angled and non-deformed state (as seen in phantom in the view of FIG. 12B), anvil (318) extends to a point even with or proximal to the distal most end of cartridge (37). When anvil (318) is deformed such that it is deflected upwardly, the end of a distal tip (319) of anvil (318) extends to a point even with or proximal to the distal most end of cartridge (37). In this manner, anvil (318) of end effector (412) remains even with or proximal to the distal most end of cartridge (37) when anvil (318) is in its angled state or deformed state such that anvil (318) does not extend past the distal most end of cartridge (37) whether anvil (318) is in its angled and non-deformed state or in its deformed state. In some instances, this can be achieved by modifying anvil (318) such that distal tip (319) of anvil is shortened in length. In other instances, instruments (10, 310) may be modified to provide for a slight proximal retraction of anvil (318) when clamping. In view of the teachings herein, other ways to modify end effector (412) as it relates to control of anvil (318) position, will be apparent to those of ordinary skill in the art.

A. Overmolded Anvil Tip

Figure 13:
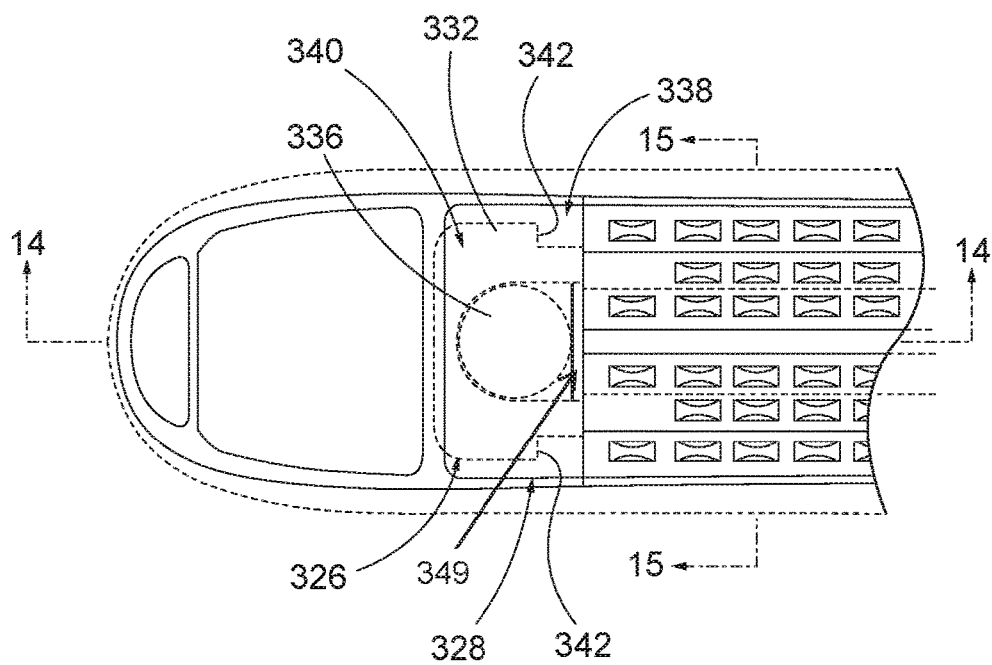
FIG. 13 depicts a bottom view of a distal portion of the end effector of FIG. 11 with the cartridge shown in phantom to reveal an underside surface of the anvil.
Figure 14:
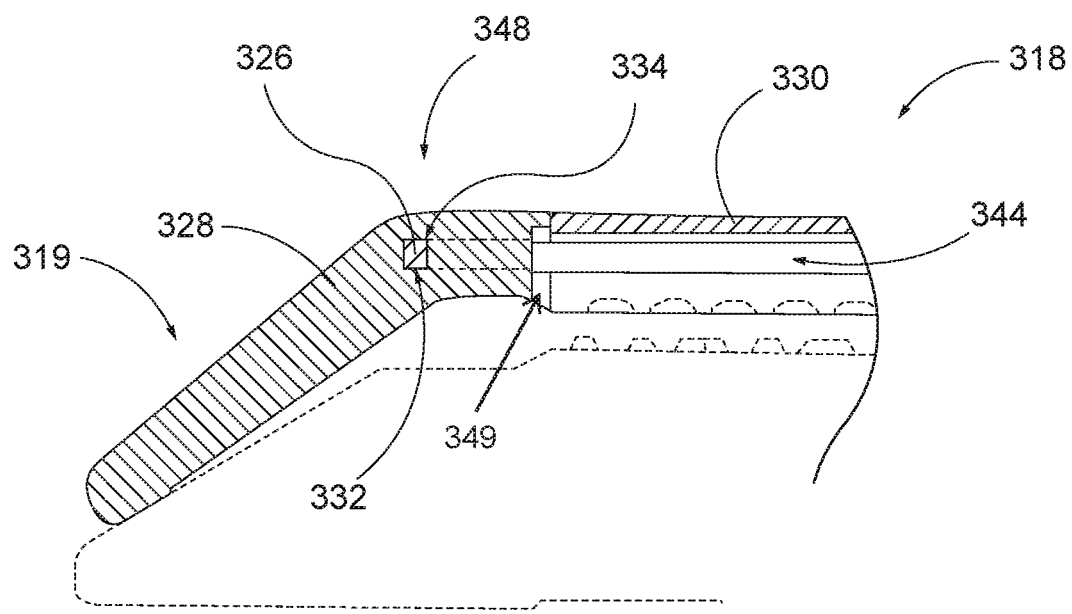
FIG. 14 depicts a side cross-sectional view of a distal portion of the end effector of FIG. 11, taken along line 14-14 of FIG. 13.
Figure 15:
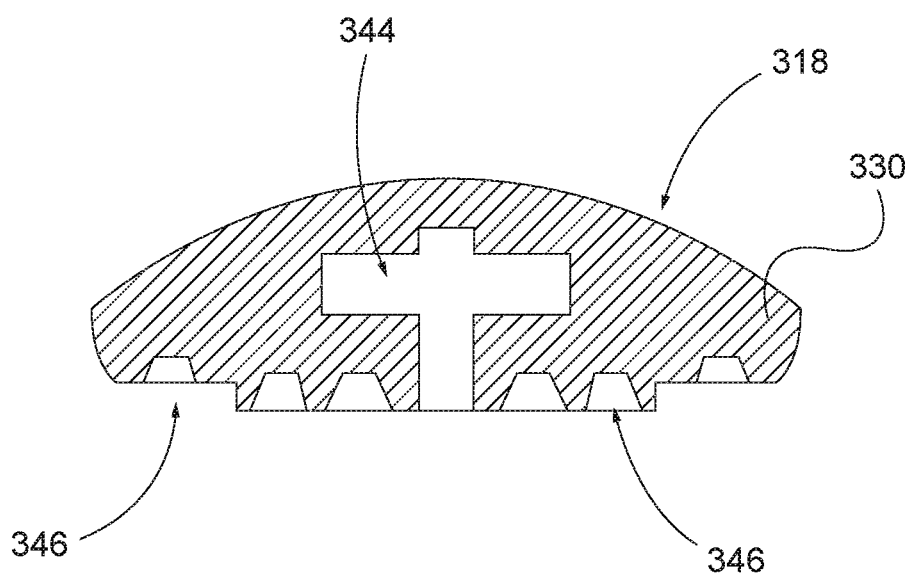
FIG. 15 depicts an end cross-sectional view of an anvil the end effector of FIG. 11, taken along line 15-15 of FIG. 13.

FIGS. 13-15 show enlarged distal views of end effector (312) to illustrate an exemplary construction. The constructions shown in FIGS. 13-15 also applies to end effector (412) shown in FIG. 12B, except for the anvil (318) length difference noted above. As shown in the top view of FIG. 13, end effector (312) comprises anvil (318) where distal tip (319) comprises a rigid portion (326) and a deflectable portion (328). In the present example, deflectable portion (328) is overmolded onto rigid portion (326) to form distal tip (319) of anvil (318). In the illustrated example as shown in FIG. 13, the outline of cartridge (37) is shown in phantom to reveal underside surface (324) of anvil (318). Rigid portion (326) of distal tip (319) extends from a body (330) of anvil (318). In the present example, body (330) is comprised of metal and rigid portion (326) is an extension of metal body (330) into distal tip (319). In other versions, body (330) and/or rigid portion (326) can be comprised of materials other than metal, including but not limited to plastic, ceramic, combinations of metal with plastic or ceramic, and other suitable materials or combinations of materials that will be apparent to those of ordinary skill in the art in view of the teachings herein. Additionally, rigid portion (326) in some versions is entirely rigid, yet in other versions rigid portion (326) can be resilient to a lesser extent than deflectable portion (328).

In the illustrated version of FIGS. 13 and 14, metal portion (326) comprises an underside surface (332) that is generally flat or planar, and a top surface (334) that is similarly generally flat or planar. Metal portion (326) further comprises an opening (336) that extends through metal portion (326) from top surface (334) to underside surface (332). Additionally, metal portion (326) comprises a neck region (338), a head region (340) that extends distally from neck region (338), and shoulders (342) at the transition between neck region (338) and head region (340). In the present example neck region (338) extends from body (330) of anvil (318). With this arrangement, metal portion (326) provides securing features or interfaces, such as opening (336) and shoulders (342), where elastomeric portion (328) can connect with metal portion (326) in a secure fashion using an overmolding process.

FIG. 15 illustrates a cross section view of anvil (318) just proximal to distal tip (319). As shown, anvil (318) comprises a longitudinal slot (344) that divides six rows of staple forming pockets (346) into two sets of three rows each. Slot (344) and staple forming pockets (346) are structurally and functionally similar to slot (42) and staple forming pockets (53) described above with respect to anvil (18). Slot (344) comprises a "t" shaped cross section as shown in FIG. 15. Referring again to FIGS. 13 and 14, opening (336) in metal portion (326) is positioned adjacent to a laterally extending portion of slot (344). In view of the teachings herein, other ways to configure metal portion (326) for suitable connection with elastomeric portion (328) using an overmolding process will be apparent to those of ordinary skill in the art.

Elastomeric portion (328) is molded onto metal portion (326) and in the molding process is imparted with an angled configuration such that elastomeric portion (328) defines a plane that intersects and is not co-planar with a plane defined by body (330) of anvil (318). In this manner, elastomeric portion (328) is formed with a bias to maintain its angled configuration unless some other force is imparted onto elastomeric portion (328) causing it to deflect from its initial angled position. During the molding process, elastomeric material flows through and fills opening (336) in metal portion (326). Elastomeric material also flows around and adjacent to shoulders (342). In this manner, elastomer portion (328) is securely connected with metal portion (326) during the overmolding process. Elastomeric portion (328) may comprise rubber, plastic, or any other suitable natural or synthetic material having the desired elastomeric properties that will allow distal tip (318) to deform when subject to force, yet resiliently return to its initial angled state when the force is no longer applied or present. During the molding process, a stop member (not shown) may be inserted into a slot (349) formed distally to slot (344), to prevent the elastomeric material from entering slot (344). In view of the teachings herein, other ways to configure elastomeric portion (328) for suitable connection with metal portion (326) using an overmolding process will be apparent to those of ordinary skill in the art.

With the configuration for distal tip (319) as described above and shown in FIGS. 13 and 14, the extension of metal portion (326) into the region of distal tip (319) defines a deflection zone (348). Deflection zone (348) coincides with a rigid portion of distal tip (319) located at a proximal end of distal tip (319). With this area of increased rigidity, distal tip (319) will deflect, for example as shown in FIG. 12A, with deflection zone (348) serving as a pivot point or location about which the remainder of distal tip (319) rotates during deflection. In view of the teachings herein, those of ordinary skill in the art will appreciate other ways in which to modify distal tip (319) to alter, modify, or control deflection zone (348) such that a desired deflection of distal tip (319) is achieved. Some such ways will be described in further detail below.

B. Anvil Tip and Cartridge with Interlocking Features

In some instances, where end effectors include anvils that incorporate a deformable distal tip that is curved or angled, features can be incorporated into the distal tip of the anvil that work cooperatively with features incorporated into the distal tip of the cartridge to provide an interlocking feature for the end effector. This interlocking feature can be particularly useful when making a final cut in a procedure that involves marching, or in procedures where a vessel is transected. For instance, when the final portion of tissue is grasped within the end effector, or when the vessel is grasped within the end effector, the distal tip of the anvil closes and contacts the distal tip of the cartridge. Features of each portion can then engage to provide the interlocking feature. This interlocking feature can provide feedback to a user indicating that the tissue or vessel being clamped is fully captured within the end effector. In other instances, the interlocking features can be useful when directing an instrument that uses this end effector configuration to a surgical site by retaining the end effector in a closed configuration such that the curved tip provides for better maneuverability through surrounding tissue while presenting an atraumatic tip to the surrounding tissue. As used herein, the terms "angled" and "curved" shall be read as being synonymous with each other when referring to a distal end configuration of a component of an end effector.

FIGS. 16 and 17 show an enlarged portion of the distal end of an exemplary end effector (512) that incorporates an interlocking feature as introduced above. It will be appreciated that end effector (512) may be used in place of end effector (12) shown in FIG. 1, or in place of end effector (312) shown in FIG. 11. In some versions, end effector (512) may be integrally formed with either shaft (22, 322) or alternatively may be separately formed and then combined. In some versions, end effector (512) may be provided for use in robotic systems as described above.

End effector (512) comprises anvil (518), lower jaw (16), and cartridge (537). Lower jaw (16) is the same structurally and functionally as described above with respect to instrument (10). Lower jaw (16) is configured to selectively receive cartridge (537). Cartridge (537) is structurally and functionally similar to cartridge (37) described above with respect to instrument (10). However, cartridge (537) incorporates dual recesses (538) at a distal tip (540) of cartridge (537). Recesses (538) each comprise an undercut feature (546). In the present example, recesses (538) with undercut features (546) are molded into distal tip (540) when forming cartridge (537). In other examples, recesses (538) and undercut features (546) may be machined into distal tip (540) after cartridge (537) is formed.

As shown in FIGS. 16 and 17, the present example includes two separate recesses (538) that extend longitudinally. Furthermore, each undercut feature (546) also extends longitudinally into distal tip (540) of cartridge (537). Each undercut feature (546) is defined by a portion of each respective recess (538). In this manner, each recess (538) comprises a base (542), sidewalls (544), and undercut feature (546). Formed between and connecting each recess (538) is a cut-out (548). The remaining features of cartridge (537) are similar to cartridge (37) as described above.

Anvil (518) comprises body (530) and distal tip (519). Distal tip (519) has an angled configuration as illustrated and described above with respect to end effectors (312, 412). In the present example, distal tip (519) is configured as a deformable tip having a rigid portion and deflectable portion (528), which are similar in structure and function to rigid portion (326) and deflectable portion (328) of anvil (312). In some other versions, distal tip (519) may be configured as angled, but rigid such that distal tip (519) is not deformable. To achieve a deformable tip configuration for distal tip (519), as in the present example, distal tip (519) can be overmolded onto body (530) of anvil (518) in the same manner as described above with respect to anvil (318). To this end, a slot (549) is formed to receive a stop member (not shown) in order to prevent the elastomeric material from entering the slot of anvil (518). As will be discussed further below, there are other structures and ways to provide a deformable tip configuration for distal tip (519) besides the overmolding configuration descried above.

Distal tip (519) of anvil (518) further comprises a latch (550) extending from an underside surface (524) of distal tip (519). Latch (550) is deformable in the present example, and is constructed of an elastomeric material. In some versions latch (550) is an overmolded feature formed during the same molding process as when deflectable portion (528) is formed. In view of the teachings herein, other materials for construction of latch (550) and other ways to form latch (550) will be apparent to those of ordinary skill in the art.

Latch (550) comprises hook members (552) on each side of latch (550). Each hook member (552) includes a tip (554) on the proximal-most end of latch (550). At each tip (554) has a chamfer (557). Latch (550) further comprises void space (556) that is located between each hook member (552). As shown in FIG. 16, latch (550) is configured to engage with undercut features (546) of cartridge (537). This engagement provides for a selective interlock between anvil (518) and cartridge (537). With the resilient nature of elastomeric latch (550) and hook members (552), when closing end effector (512) to engage anvil (518) with cartridge (537), hook members (552) will deflect when contacting a tapered surface (539) of distal tip (540). Hook members (552) may also deflect upon contacting a vertical face (547) of undercut features (546). This deflection will allow anvil (518) to continue to close and allow hook members (552) to engage within undercut features (546). In the present example, each hook member (552) comprises chamfer (556) that first contacts tapered surface (539) and/or vertical face (547) to promote gradual deflection of hook members (552) when engaging anvil (518) with cartridge (537).

From an engaged position as shown in FIG. 16, anvil (518) can be separated from cartridge (537) by providing an opening force sufficient to overcome the bias of hook members (552) such that they deform and disengage from undercut features (546) of recesses (538). Instead or in addition, anvil (518) can be separated from cartridge (537) by providing an opening force sufficient to deflect distal tip (519) such that hook members (552) disengage from undercut features (546). For instance, the deformability of hook members (552) and the remainder of distal tip (519) can be configured such that hook members (552) will deflect more easily than the remainder of distal tip (519). In this configuration, hook members (552) will deflect first to disengage anvil (518) from cartridge (537). Conversely, the deformability of hook members (552) and the remainder of distal tip (519) can be configured such that hook members (552) will deflect less easily than the remainder of distal tip (519). In this configuration, the portions of distal tip (519) other than hook members (552) will deflect first to ultimately disengage anvil (518) from cartridge (537). Still yet, the deformability of hook members (552) and the remainder of distal tip (519) can be configured such that hook members (552) will deflect as easily as than the remainder of distal tip (519). In this configuration, both the portions of distal tip (519) and hook members (552) will deflect to ultimately disengage anvil (518) from cartridge (537).

When latch (550) engages with undercut features (546), a distal portion (558) of latch (550) is configured to fit within cut-out (548) of cartridge (537). Likewise, void space (556) is configured to receive a proximal portion (560) of a dividing wall (562) that separates and defines recesses (538). In this manner, hook members (552) are insertable in a longitudinal direction deep enough within each recess (538) to reach and ultimately engage with undercut features (546). With this configuration for latch (550) and distal tip (540) of cartridge (537), end effector (512) comprises four complementary features between anvil (518) and cartridge (537). Two such complementary features being each hook member (552) and each respective undercut feature (546), another complementary feature being cut-out (548) and distal portion (558) of latch (550), and the fourth complementary feature being void space (556) and proximal portion (560) of dividing wall (562).

As described above, and as illustrated in FIGS. 16 and 17, the interlocking feature is configured such that the engagement between undercut features (546) and hook members (552) of latch (550) is oriented longitudinally. In other words, hook members (552) of latch (550) extend longitudinally toward the proximal end of end effector (512). Similarly, the recesses (538) extend longitudinally as well as undercut features (546). Therefore, undercut features (546) are engaged by hook members (552) from a longitudinal direction. Disengagement, when anvil (518) is separated from cartridge (537), occurs in the reverse manner as described above, and such disengagement occurs through deflection that occurs along a longitudinal axis of cartridge (537).

Figure 18:
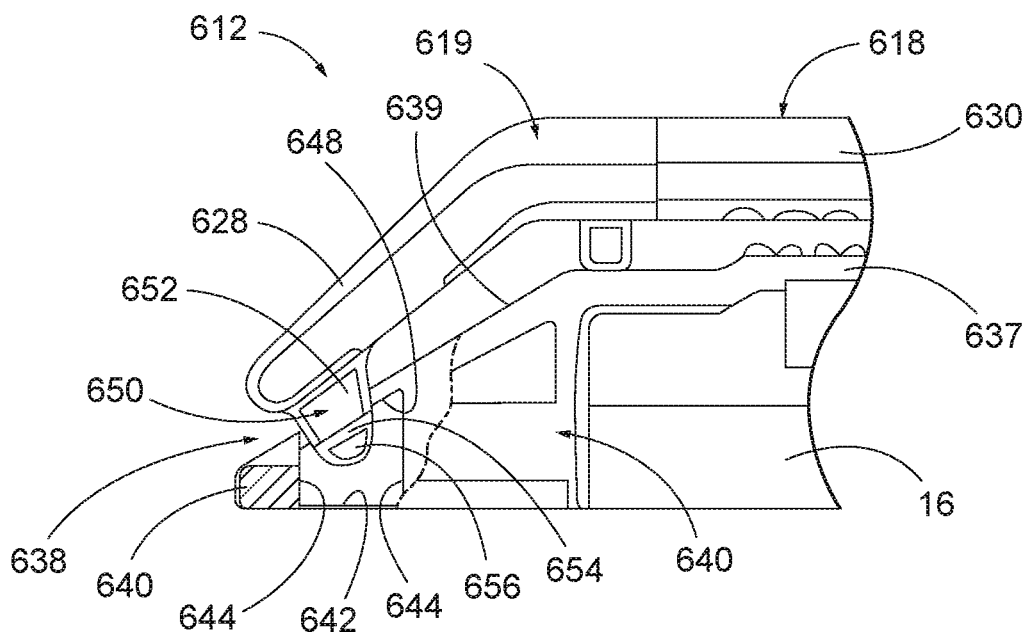
FIG. 18 depicts an enlarged side view of a distal portion of another exemplary alternative end effector for use with the surgical stapling instruments described herein, shown in partial cross-section to reveal internal features.
Figure 19:
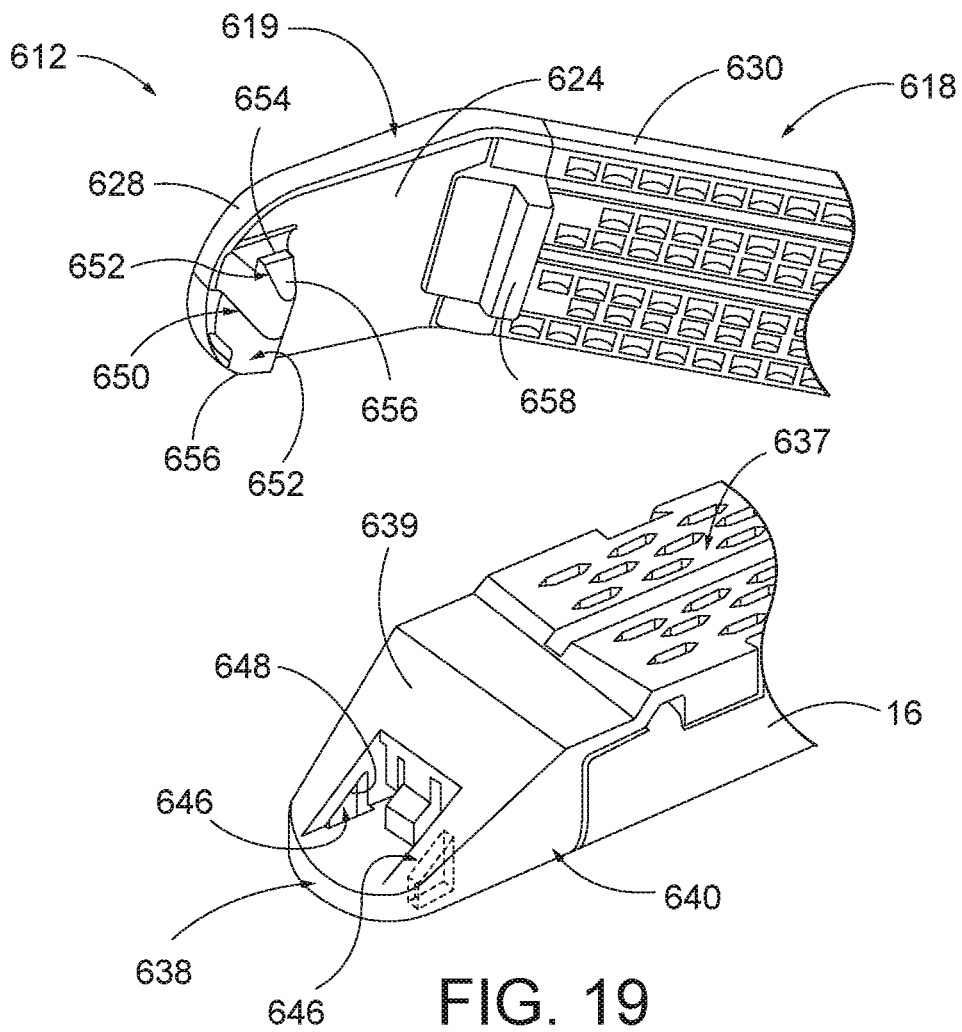
FIG. 19 depicts an exploded perspective view of a distal portion of the end effector of FIG. 18.

FIGS. 18 and 19 show an enlarged portion of the distal end of another exemplary end effector (612) that incorporates an interlocking feature. It will be appreciated that end effector (612) may be used in place of end effector (12) shown in FIG. 1, or in place of end effector (312) shown in FIG. 11. In some versions, end effector (612) may be integrally formed with either shaft (22, 322) or alternatively may be separately formed and then combined. In some versions, end effector (612) may be provided for use in robotic systems as described above.

End effector (612) comprises anvil (618), lower jaw (16), and cartridge (637). Lower jaw (16) is the same structurally and functionally as described above with respect to instrument (10). Lower jaw (16) is configured to selectively receive cartridge (637). Cartridge (637) is structurally and functionally similar to cartridge (37) described above with respect to instrument (10). However, cartridge (637) incorporates a recess (638) at a distal tip (640) of cartridge (637). Recess (638) comprises undercut features (646). In the present example, recess (638) with undercut features (646) are molded into distal tip (640) when forming cartridge (637). In other examples, recess (638) and undercut features (646) may be machined into distal tip (640) after cartridge (637) is formed.

As shown in FIGS. 18 and 19, recess (638) extends longitudinally into distal tip (640) of cartridge (637). Each undercut feature (646) extends into distal tip (640) of cartridge (637) orthogonally relative to a longitudinal axis defined by cartridge (637). Each undercut feature (646) comprises a base (642), sidewalls (644), and a top surface (648). Each top surface (648) defines a plane that is parallel to a plane defined by a tapered surface (639) of cartridge (637). In this manner, each undercut feature (646) comprises a tapered profile. However, in some other versions, undercut features can have a straight profile instead. The remaining features of cartridge (637) are similar to cartridge (37) as described above. In view of the teachings herein, other ways to form recess (638) and undercut features (646) will be apparent to those of ordinary skill in the art.

Anvil (618) comprises body (630) and distal tip (619). Distal tip (619) has an angled configuration as illustrated and described above with respect to end effectors (312, 412, 512). In the present example, distal tip (619) is configured as a deformable tip having a rigid portion and deflectable portion (628), which are similar in structure and function to rigid portion (326) and deflectable portion (328) of anvil (312). In some other versions, distal tip (619) may be configured as angled, but rigid such that distal tip (619) is not deformable. To achieve a deformable tip configuration for distal tip (619), as in the present example, distal tip (619) can be overmolded onto body (630) of anvil (618) in the same manner as described above with respect to anvil (318). As will be discussed further below, there are other structures and ways to provide a deformable tip configuration for distal tip (619) besides the overmolding configuration descried above.

Distal tip (619) of anvil (618) further comprises a latch (650) extending from an underside surface (624) of distal tip (619). Latch (650) is deformable in the present example, and is constructed of an elastomeric material. In some versions latch (650) is an overmolded feature formed during the same molding process as when deflectable portion (628) is formed. In view of the teachings herein, other materials for construction of latch (650) and other ways to form latch (650) will be apparent to those of ordinary skill in the art.

Latch (650) comprises hook members (652) on each side of latch (650). Each hook member (652) extends outwardly from latch (650) orthogonally relative to a longitudinal axis of anvil (618). Each hook member (652) includes a tip (654) at its end. Each tip (654) is configured to engage with a respective undercut feature (646) of cartridge (637) as shown in FIG. 18. This engagement provides for a selective interlock between anvil (618) and cartridge (637). With the resilient nature of elastomeric latch (650) and hook members (652), when closing end effector (612) to engage anvil (618) with cartridge (637), hook members (652) will deflect when contacting the sidewalls of recess (638). This deflection will allow anvil (618) to continue to close and allow hook members (652) to engage within undercut features (646). In the present example, each hook member (652) comprises a chamfer (656) that contacts the sidewalls of recess (638) to promote gradual deflection of hook members (652) when engaging anvil (618) with cartridge (637).

As shown and described in the present example, a width of latch (650) can be defined as the distance from the end of one hook member (652) to the end of the other hook member (652). Similarly, a width of recess (638) can be defined as the distance from one sidewall of recess (638) to the opposing sidewall of recess (638). In the present example, the width of latch (650) is greater than the width of recess (638). However, undercut features (646) provide for additional width within recess (638). Furthermore, the resilient nature of latch (650) allows for hook members (652) of latch (650) to deform inwardly such that the width of latch (650) can be reduced during closure of end effector (612) to permit engagement of hook members (652) with undercut features (646). Upon engagement, the width of latch (650) may return to its initial width thereby promoting a secure but selective connection between anvil (518) and cartridge (637).

From an engaged position as shown in FIG. 18, anvil (618) can be separated from cartridge (637) by providing an opening force sufficient to overcome the bias of hook members (652) such that they deform and disengage from undercut features (646) of cartridge (637). Instead or in addition, anvil (618) can be separated from cartridge (637) by providing an opening force sufficient to deflect distal tip (619) such that hook members (652) disengage from undercut features (646). For instance, the deformability of hook members (652) and the remainder of distal tip (619) can be configured such that hook members (652) will deflect more easily than the remainder of distal tip (619). In this configuration, hook members (652) will deflect first to disengage anvil (618) from cartridge (637). Conversely, the deformability of hook members (652) and the remainder of distal tip (619) can be configured such that hook members (652) will deflect less easily than the remainder of distal tip (619). In this configuration, the portions of distal tip (619) other than hook members (652) will deflect first to ultimately disengage anvil (618) from cartridge (637). Still yet, the deformability of hook members (652) and the remainder of distal tip (619) can be configured such that hook members (652) will deflect as easily as than the remainder of distal tip (619). In this configuration, both the portions of distal tip (619) and hook members (652) will deflect to ultimately disengage anvil (618) from cartridge (637).

As described above, and as illustrated in FIGS. 18 and 19, the interlocking feature is configured such that the engagement between undercut features (646) and hook members (652) of latch (650) is oriented orthogonally relative to a longitudinal axis of cartridge (637). In other words, hook members (652) of latch (650) extend transversely away from a longitudinal axis of cartridge (637). Similarly, recess (638) extends longitudinally while undercut features (646) extend orthogonally relative to a longitudinal axis of cartridge (637). Therefore, undercut features (646) are engaged by hook members (652) from a transverse direction, or direction that is generally orthogonal to the longitudinal axis defined by cartridge (637). Disengagement, when anvil (618) is separated from cartridge (637), occurs in the reverse manner as described above, and such disengagement occurs through deflection that occurs generally orthogonally to a longitudinal axis of cartridge (637).

Anvil (618) of end effector (612) further comprises a gap setting feature (658). Gap setting feature (658) is located at the proximal end of distal tip (619). Gap setting feature (658) is sized such that it contacts an anvil-facing surface of cartridge (637) when end effector (612) is in a closed configuration as shown in FIG. 18. Furthermore, when gap setting feature (658) contacts cartridge (637), tips (654) of hook members (652) of latch (650) contact top surface (648) of respective undercut features (646). In this manner, when anvil (618) is engaged with cartridge (637), further closure of anvil (618) is restricted by gap setting feature (658). In the illustrated example of FIGS. 18 and 19, gap setting feature (658) comprises a rectangular beam shape; however, other shapes and configurations for gap setting feature (658) will be apparent to those of ordinary skill in the art in view of the teachings herein.

C. Anvil with Deformable Tip and Tissue Stabilizing Features

In some instances, where end effectors include anvils that incorporate an angled and deformable distal tip, features can be incorporated into the distal tip of the anvil that aid in stabilizing tissue that is clamped between the anvil and cartridge of the end effector. These tissue stabilizing features can be particularly useful when the end effector is being used in a procedure that involves marching. In particular, it can be helpful to stabilize the tissue to ensure the current cut is executed as intended while maintaining a projected cut line for the next cuts in the sequence. Additionally, the tissue stabilizing features may be comprised from an elastomeric material that is resiliently deformable. The combination of providing tissue stabilizing features on an anvil tip that is also angled and deformable can provide a way to improve tissue capture and retention while also providing a way to handle captured tissue with less chance of tissue trauma because of the deformability features of the anvil distal tip and tissue stabilizing features.

Figure 20:
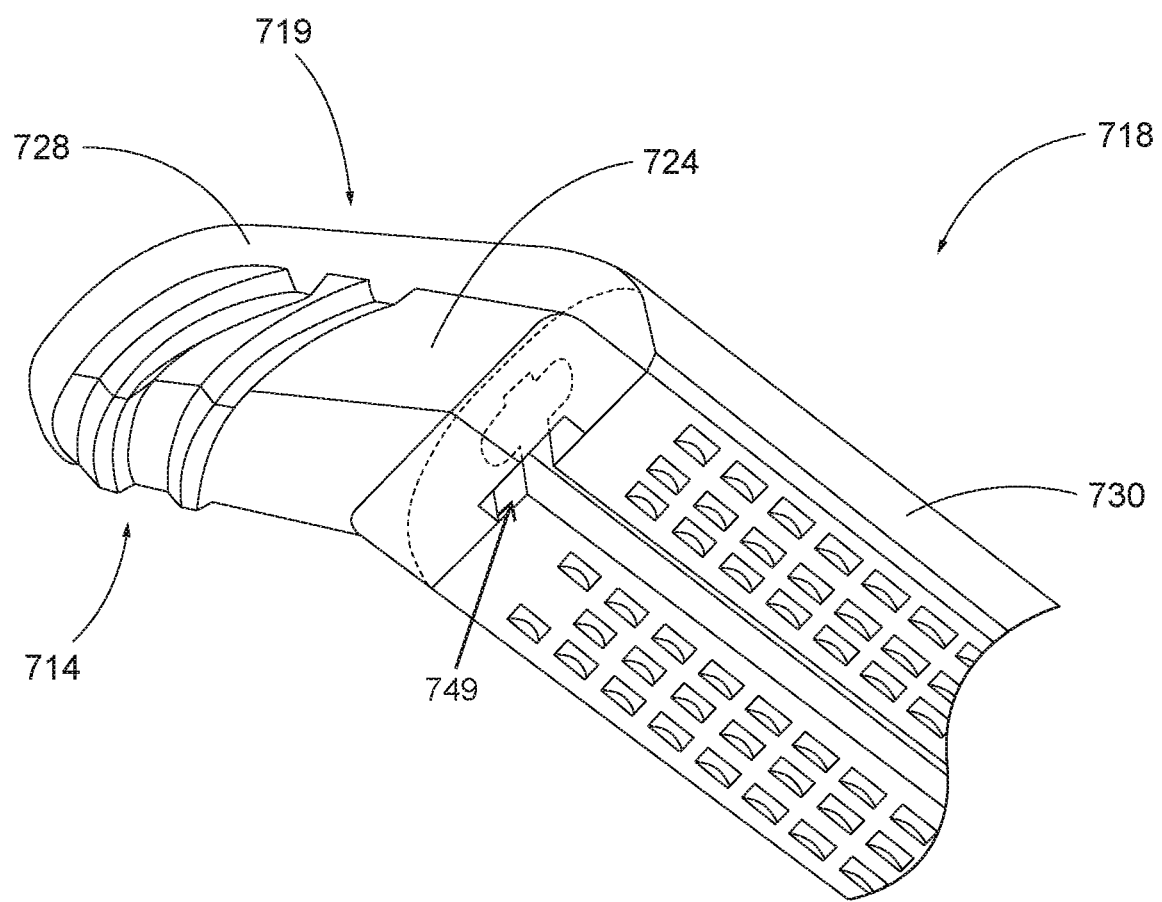
FIG. 20 depicts an enlarged perspective view of a distal portion of an exemplary alternative anvil for an end effector for use with the surgical stapling instruments described herein.

FIG. 20 shows an enlarged portion of a distal end of another exemplary anvil (718) of an end effector where anvil (718) incorporates tissue stabilizing features (714). Anvil (718) comprises a body (730) and a distal tip (719) connected with the body (730). It will be appreciated that anvil (718) can be paired with lower jaw (16) and cartridge (37) to provide the end effector for an instrument such as instruments (10, 310). Similarly, anvil (718) may be used in place of anvil (18) in end effector (12), or in place of anvil (218) in end effector (212), or in place of anvil (318) in end effectors (312, 412).

In the present example, tissue stabilizing features (714) are configured as two arcuate ridges located at a distal end of distal tip (719) of anvil (718). In other versions, greater or fewer number of tissue stabilizing features (714) may be used. Also, in other versions, tissue stabilizing features (714) may be configured with alternate shapes or locations along an underside surface (724) of anvil (718).

Tissue stabilizing features (714) are further formed as part of a deflectable portion (728) of distal tip (719). In the present example, deflectable portion (728) and tissue stabilizing features (714) are formed from an elastomeric material. Furthermore, tissue stabilizing features (714) may be formed in a molding process during formation of the remainder of deflectable portion (728). To this end, a slot (749) is formed to receive a stop member (not shown) in order to prevent the elastomeric material from entering the slot of anvil (718). With this configuration as shown and described, anvil (718) is provided with an angled deformable distal tip (719) having one or more resilient tissue stabilizing features (714). In view of the teachings herein, other configurations for angled and deformable distal tip (719) for anvil (718) having resilient tissue stabilizing features (714) will be apparent to those of ordinary skill in the art.

IV. CURVED ELASTICALLY DEFORMABLE ANVIL TIPS WITH RIGID ENDS

As discussed above, in some instances, it may be desirable to provide the user with a variation of end effector (12, 212) that provides the marching capabilities of end effector (12), the improved visibility associated with end effector (212), and the tissue gathering capabilities of end effector (212), without providing an increased risk of trauma that might otherwise be associated with fully rigid versions of end effector (212). In some instances, it may be desirable to provide for an angled and deformable anvil tip while also maintaining a rigid distal end of the anvil. With this configuration, the end effector may provide the additional benefit of having a dissection end in an end effector configuration that provides for the enhanced visualization, maneuverability, and tissue gathering capabilities as described above. In addition or in the alternative, providing a rigid portion in the distal end of an end effector may aid in insertion of the end effector into tight spaces, dilating openings, etc. While providing such capabilities, it may also be desirable to maintain at least some degree of elasticity to allow deformation in response to substantial transverse loads.

A. Anvil with Thin Profile Nose

Figure 21:
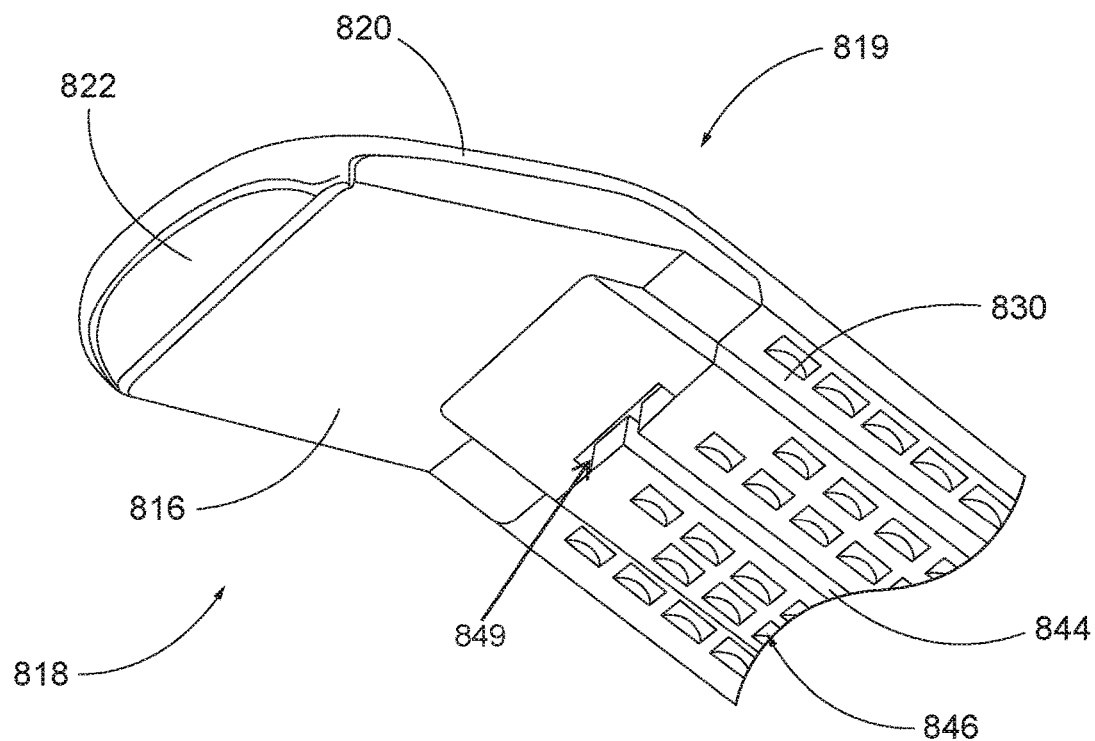
FIG. 21 depicts an enlarged perspective view of a distal portion of another exemplary alternative anvil for an end effector for use with the surgical stapling instruments described herein.
Figure 22:
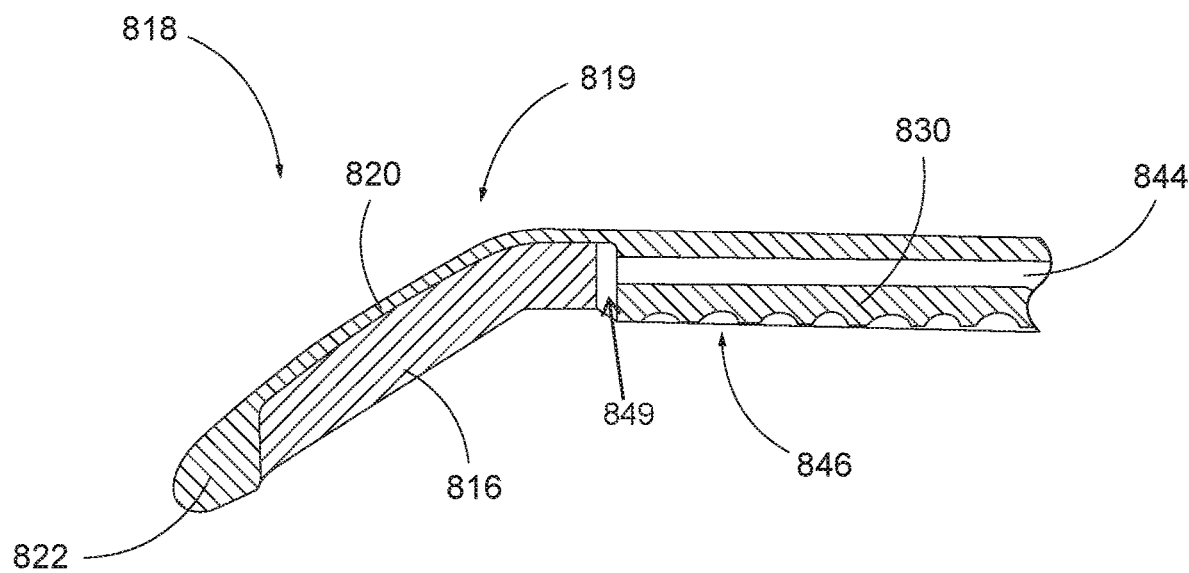
FIG. 22 depicts a side cross sectional view of a distal portion of the anvil of FIG. 21.

FIGS. 21 and 22 show an exemplary anvil (818) for an end effector. It will be appreciated that anvil (818) can be paired with lower jaw (16) and cartridge (37) to provide the end effector for an instrument such as instruments (10, 310). Similarly, anvil (818) may be used in place of anvil (18) in end effector (12), or in place of anvil (218) in end effector (212), or in place of anvil (318) in end effectors (312, 412). Anvil (818) comprises body (830) and curved distal tip (819). Anvil (818) further comprises staple forming pockets (846) and slot (844), which are structurally and functionally similar to staple forming pockets (53) and slot (49) described above.

In the present example, body (830) comprises a metallic material of rigid construction. Curved distal tip (819) extends distally from body (830). Curved distal tip (819) comprises an elastomeric pad (816), nose portion (820), and distal end (822). Nose portion (820) connects with and extends from body (830) and is of the same metallic material of construction. Distal end (822) connects with and extends from nose portion (820) and is also of the same metallic material of construction. In this manner, both nose portion (820) and distal end (822) can be considered extensions of body (830) formed as part of curved distal tip (819). Nose portion (820) comprises a thin profile that allows for and promotes deflection of nose portion (820) of anvil (818). In the present example, nose portion (820) defines a deflection zone. Distal end (822) comprises a thick profile such that distal end (822) is rigid and any deflection at distal end (822) is due to the deflection of nose portion (820) as mentioned. In this manner, distal end (822) may be operatively configured for dissecting tissue or vessels.

Elastomeric pad (816) connects with an underside surface of nose portion (820). This connection may be achieved chemically or mechanically; and in view of the teachings herein those of ordinary skill in the art will appreciate the various ways to connect pad (816) with the remainder of anvil (818). In some versions, elastomeric pad (816) is bonded to anvil (818) using a molding process. In such examples, the underside of nose portion (820) may comprise structural features configured to engage with pad (816) during molding to thereby secure pad (816) to anvil (818). By way of example only, and not limitation, anvil (818) may be configured with a rigid portion similar to rigid portion (326) of anvil (318). In such an example, pad (816) may be overmolded with the rigid portion similar to the overmolding of deflectable portion (328) to rigid portion (326) as shown and described above with respect to FIGS. 13-15. To this end, a slot (849) is formed to receive a stop member (not shown) in order to prevent the elastomeric material from entering slot (844) of anvil (818).

In another version of anvil (818), body (830), nose portion (820), and distal end (822) can be constructed of another suitable material other than a metallic material. By way of example, and not limitation, other suitable materials may include various plastics, among others that will be apparent to those of ordinary skill in the art in view of the teachings herein. Accordingly, while the above example describes a metallic construction for body (830), nose portion (820), and distal end (822), the construction of anvil (818) should not be limited to a metallic construction.

B. Anvil with Elastomeric Insert

Figure 23:
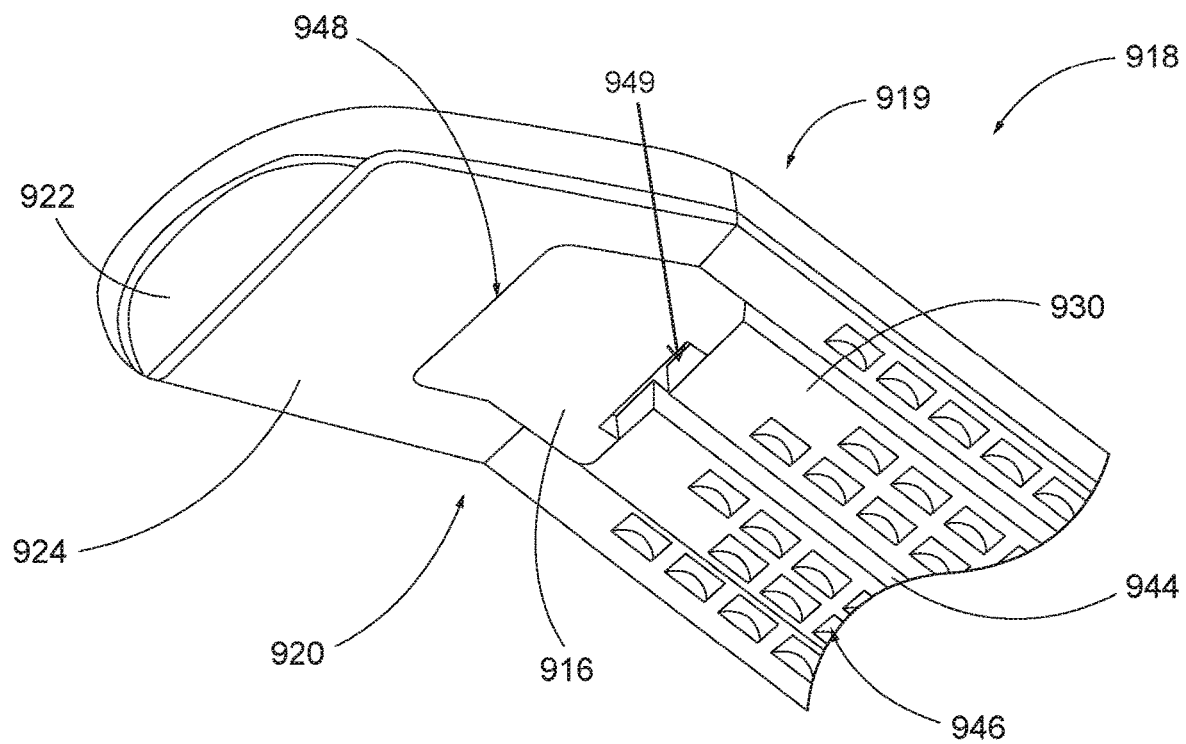
FIG. 23 depicts an enlarged perspective view of a distal portion of another exemplary alternative anvil for an end effector for use with the surgical stapling instruments described herein.
Figure 24:
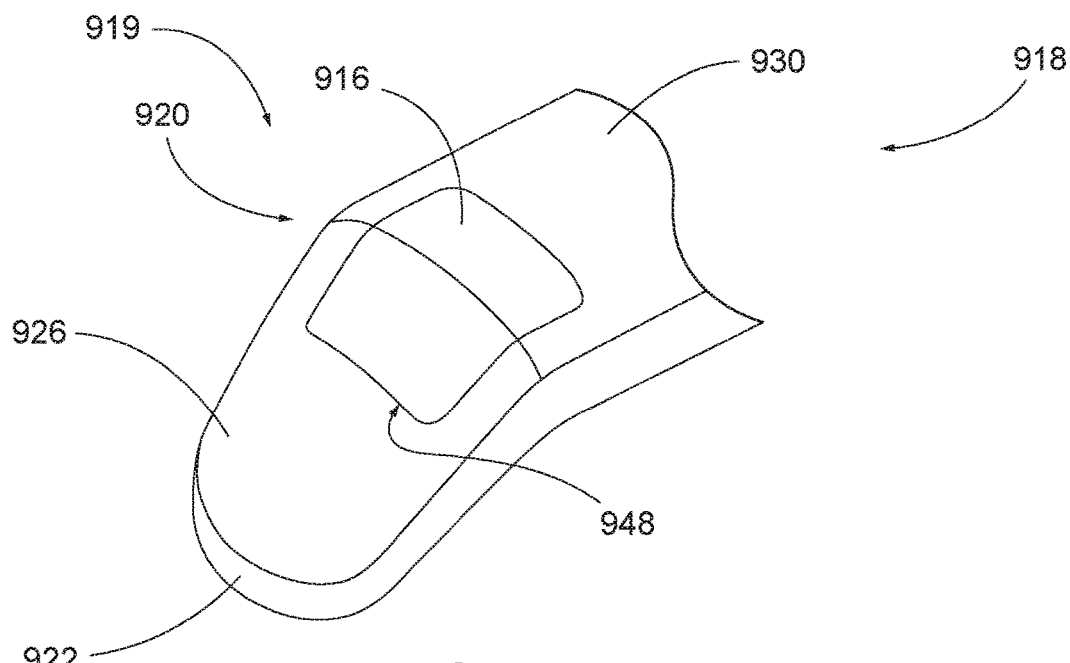
FIG. 24 depicts another enlarged perspective view of a distal portion of the anvil of FIG. 23.

FIGS. 23 and 24 show an exemplary anvil (918) for an end effector. It will be appreciated that anvil (918) can be paired with lower jaw (16) and cartridge (37) to provide the end effector for an instrument such as instruments (10, 310). Similarly, anvil (918) may be used in place of anvil (18) in end effector (12), or in place of anvil (218) in end effector (212), or in place of anvil (318) in end effectors (312, 412). Anvil (918) comprises body (930) and curved distal tip (919). Anvil (918) further comprises staple forming pockets (946) and slot (944), which are structurally and functionally similar to staple forming pockets (53) and slot (49) described above.

In the present example, body (930) comprises a metallic material of rigid construction. Curved distal tip (919) extends distally from body (930). Curved distal tip (919) comprises an elastomeric insert (916), nose portion (920), and distal end (922). Nose portion (920) connects with and extends from body (930) and is of the same metallic material of construction. Distal end (922) connects with and extends from nose portion (920) and is also of the same metallic material of construction. In this manner, both nose portion (920) and distal end (922) can be considered extensions of body (930) formed as part of curved distal tip (919). Nose portion (920) comprises an opening (948) that extends from a top surface (926) of nose portion (920) to an underside surface (924) of nose portion (920). Elastomeric insert (916) is configured such that it fits within and fills opening (948), and this configuration allows for and promotes deflection of nose portion (920) of anvil (918). In the present example, elastomeric insert (916) defines a deflection zone. Distal end (922) comprises a thick profile such that distal end (922) is rigid and any deflection at distal end (922) is due to the deflection of nose portion (920) about elastomeric insert (916) as mentioned. In this manner, distal end (922) may be operatively configured for dissecting tissue or vessels. Additionally, distally adjacent to elastomeric insert (916), is underside surface (924) of nose portion (920). Underside surface (924) is generally flat and transitions to distal end (922), which is illustrated with a chamfer surface. With this configuration, underside surface (924) may provide for additional contact area beyond distal end (922) for dissection of tissue or vessels. It should be understood that insert (916) may be molded or may be formed as one or more separate piece(s) that is/are later joined to anvil (918).

As mentioned, elastomeric insert (916) fills opening (948) within nose portion (920) of curved distal tip (919). Elastomeric insert (916) may connect nose portion (920) using a chemical or mechanical fastening. In view of the teachings herein those of ordinary skill in the art will appreciate the various ways to connect insert (916) with the remainder of anvil (918). In some versions, elastomeric insert (916) is bonded to anvil (918) using a molding process. To this end, a slot (949) is formed to receive a stop member (not shown) in order to prevent the elastomeric material from entering slot (944) of anvil (918). It should also be understood that opening (948) of nose portion (920) may comprise various structural features configured to engage with insert (916) during molding to thereby secure insert (916) to anvil (918).

In another version of anvil (918), body (930), nose portion (920), and distal end (922) can be constructed of another suitable material other than a metallic material. By way of example, and not limitation, other suitable materials may include various plastics, among others that will be apparent to those of ordinary skill in the art in view of the teachings herein. Accordingly, while the above example describes a metallic construction for body (930), nose portion (920), and distal end (922), the construction of anvil (918) should not be limited to a metallic construction.

C. Anvil with Connection Member for Improved Deformability

Figure 25:
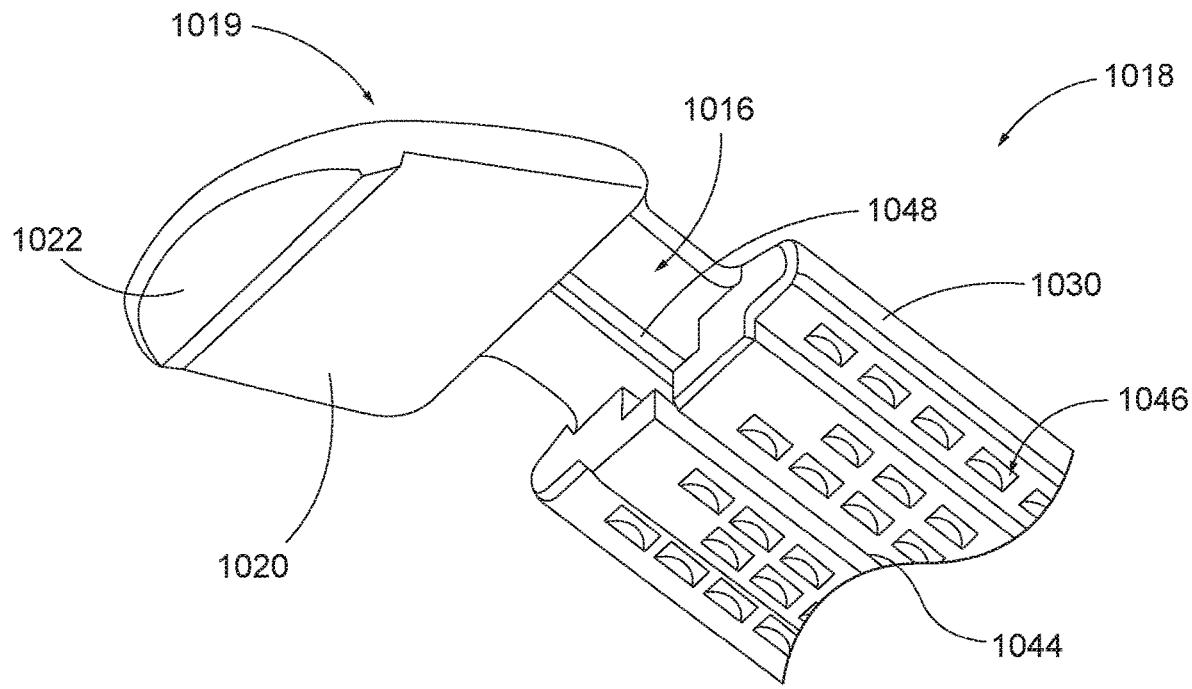
FIG. 25 depicts an enlarged perspective view of a distal portion of another exemplary alternative anvil for an end effector for use with the surgical stapling instruments described herein.
Figure 26:
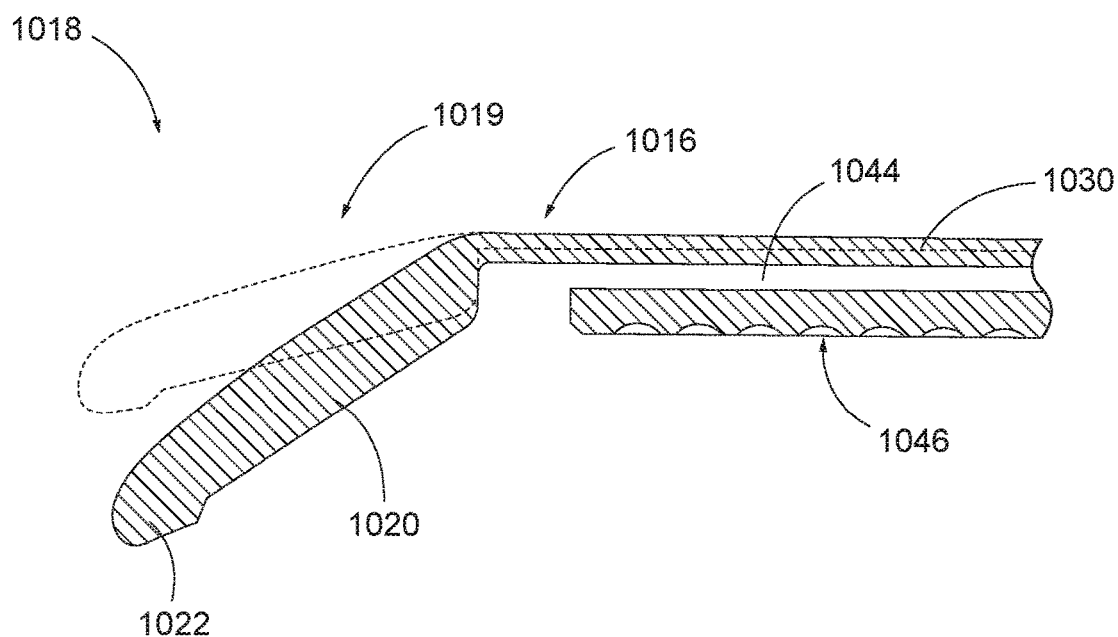
FIG. 26 depicts a side cross sectional view of a distal portion of the anvil of FIG. 25.

FIGS. 25 and 26 show an exemplary anvil (1018) for an end effector. It will be appreciated that anvil (1018) can be paired with lower jaw (16) and cartridge (37) to provide the end effector for an instrument such as instruments (10, 310). Similarly, anvil (1018) may be used in place of anvil (18) in end effector (12), or in place of anvil (218) in end effector (212), or in place of anvil (318) in end effectors (312, 412). Anvil (1018) comprises body (1030), curved distal tip (1019), and connection member (1016). Anvil (1018) further comprises staple forming pockets (1046) and slot (1044), which are structurally and functionally similar to staple forming pockets (53) and slot (49) described above.

In the present example, body (1030) comprises a metallic material of rigid construction. Connection member (1016) extends distally from body (1030) and comprises the same metallic material of construction. Curved distal tip (1019) extends distally from connection member (1016) and further comprises the same metallic material of construction. Curved distal tip (1019) comprises a nose portion (1020) and distal end (1022). Nose portion (1020) connects with and extends from connection member (1016). Distal end (1022) connects with and extends from nose portion (1020). With this configuration, both curved distal tip (1019) and connection member (1016) can be considered extensions of body (1030). Connection member (1016) comprises a thin profile that allows for and promotes deflection of nose portion (1020). In the present example, connection member (1016) defines a deflection zone for curved distal tip (1019). Curved distal tip (1019) comprises a thick profile such that nose portion (1020) and distal end (1022) are rigid and any deflection thereof is due to the deflection about connecting member (1016) as mentioned. With the thicker profile of curved distal tip (1019), distal curved tip (1019) may be operatively configured for dissecting tissue or vessels.

In addition to its thin profile, connection member (1016) comprises additional features that promote or improve the deformability of curved distal tip (1019). One such feature includes a narrower width for connection member (1016) relative to the width of body (1030) and nose portion (1020) of curved distal tip (1019). Another feature configured to improve deformability of curved distal tip (1019) comprises a slot (1048) that extends longitudinally along a midline of connection member (1016). Both slot (1048) and the narrower width of connection member (1016) are configured to reduce the rigidity of connection member (1016) such that connection member (1016) is more easily able to deflect as shown in FIG. 26 when subjected to force from either clamping or otherwise contacting tissue. In view of the teachings herein, other ways to modify connection member (1016) to remove material in order to improve deformability will be apparent to those of ordinary skill in the art.

In another version of anvil (1018), one or more of body (1030), curved distal tip (1019), and/or connection member (1016) can be constructed of another suitable material other than a metallic material. By way of example, and not limitation, other suitable materials may include various plastics, among others that will be apparent to those of ordinary skill in the art in view of the teachings herein. Accordingly, while the above example describes a metallic construction for body (1030), curved distal tip (1019), and connection member (1016), the construction of anvil (1018) should not be limited to a metallic construction.

D. Anvil with Integrated Elastomeric Contacting Pad and Rigid End

Figure 27:
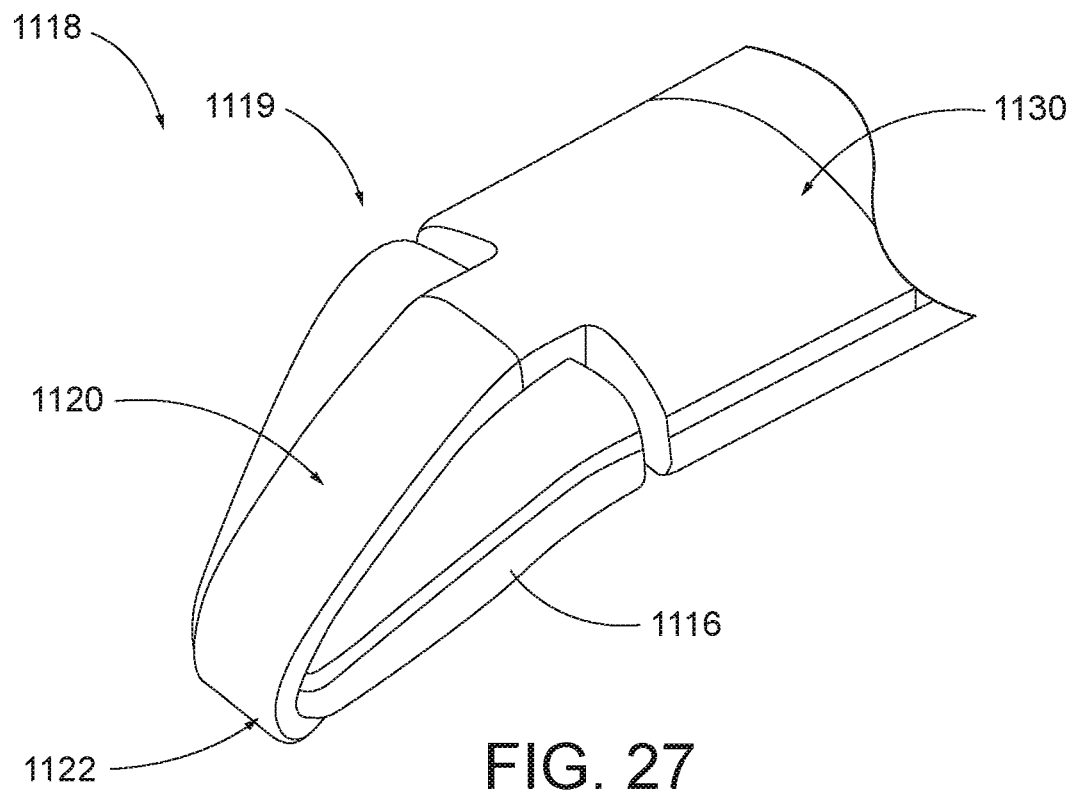
FIG. 27 depicts an enlarged perspective view of a distal portion of another exemplary alternative anvil for an end effector for use with the surgical stapling instruments described herein.
Figure 28:
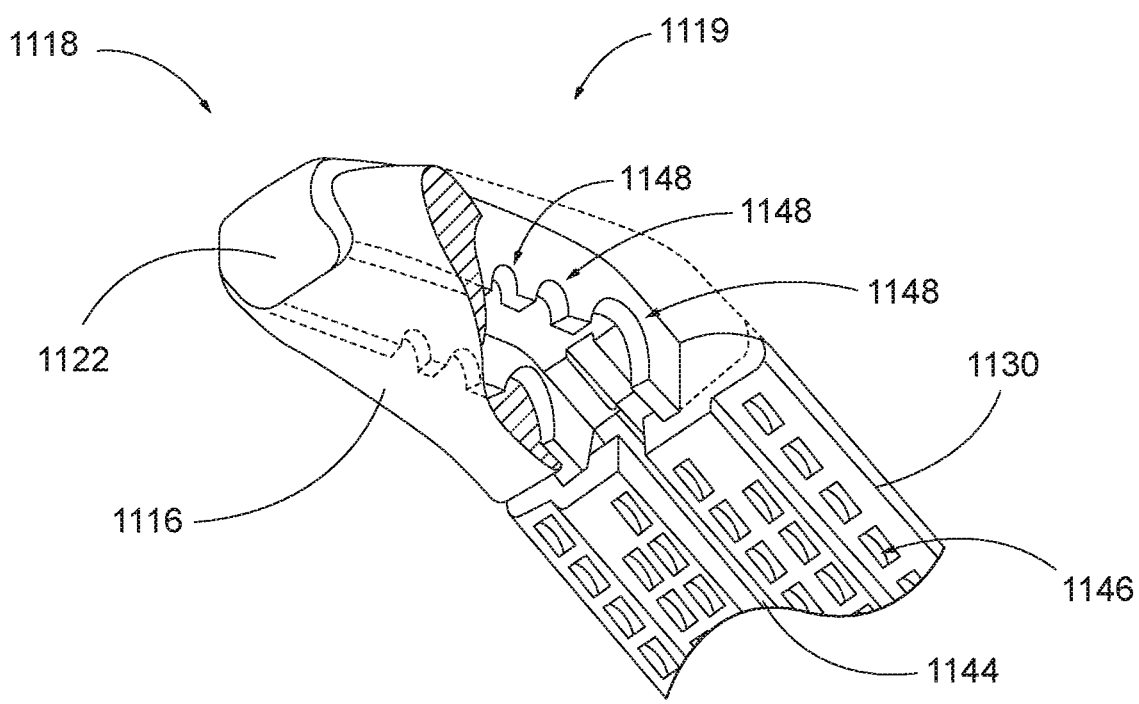
FIG. 28 depicts another enlarged perspective view of a distal portion of the anvil of FIG. 27, shown with a portion in phantom to reveal internal features.

FIGS. 27 and 28 show an exemplary anvil (1118) for an end effector. It will be appreciated that anvil (1118) can be paired with lower jaw (16) and cartridge (37) to provide the end effector for an instrument such as instruments (10, 310). Similarly, anvil (1118) may be used in place of anvil (18) in end effector (12), or in place of anvil (218) in end effector (212), or in place of anvil (318) in end effectors (312, 412). Anvil (1118) comprises body (1130) and curved distal tip (1119). Anvil (1118) further comprises staple forming pockets (1146) and slot (1144), which are structurally and functionally similar to staple forming pockets (53) and slot (49) described above.

In the present example, body (1130) comprises a metallic material of rigid construction. Curved distal tip (1119) extends distally from body (1130). Curved distal tip (1119) comprises an elastomeric pad (1116), nose portion (1120), and distal end (1122). Nose portion (1120) connects with and extends from body (1130) and is of the same metallic material of construction. Nose portion (1120) is configured with a narrower width compared to the width of body (1130) or the width of elastomeric pad (1116). As shown in FIG. 28, nose portion (1120) further comprises a plurality of notches (1148) that extend transversely across the width of nose portion (1120). Notches (1148) are configured in various sizes as nose portion (1120) extends distally. For instance, the proximal-most notch in the illustrated version is configured as the largest notch, with the distal-most notch configured as the smallest notch. Controlling the size of notches (1148) promotes improved deformability of curved distal tip (1119).

Distal end (1122) connects with and extends from nose portion (1120) and is also of the same metallic material of construction. In this manner, both nose portion (1120) and distal end (1122) can be considered extensions of body (1130) formed as part of curved distal tip (1119). As shown in the illustrated example, distal end (1122) has a width that generally matches the width of nose portion (1120). In this manner, both nose portion (1120) and distal end (1122) are configured with a narrower width compared to the width of body (1130) or the width of elastomeric pad (1116). Distal end (1122) further provides anvil (1118) with a metallic distal contact zone.

In the present example, elastomeric pad (1116) is overmolded onto nose portion (1120). During the overmolding process, elastomeric material of pad (1116) fills the spaces defined by plurality of notches (1148) and extends along side portions of nose portions (1120). In its finished molded state, elastomeric pad (1116) is configured such that there remain exposed areas of nose portion (1120) and distal end (1122) that are proud relative to elastomeric pad (1116) as shown in the illustrated example. In view of the teachings herein, other various modifications that could be made to nose portion (1120) to provide for additional or other structural features beyond notches (1148) for overmolding elastomeric pad (1116) thereto will be apparent to those of ordinary skill in the art. In some versions, tissue stabilizing features may be molded into elastomeric pad (1116). For instance, such tissue stabilizing features may be the same or similar to tissue stabilizing features (714) described above. However, other configurations for, and methods for providing, tissue stabilizing features will be apparent to those of ordinary skill in the art in view of the teachings herein.

In another version of anvil (1118), body (1130) and curved distal tip (1119) can be constructed of another suitable material other than a metallic material. By way of example, and not limitation, other suitable materials may include various plastics, among others that will be apparent to those of ordinary skill in the art in view of the teachings herein. Accordingly, while the above example describes a metallic construction for body (1130), nose portion (1120), and distal end (1122), the construction of anvil (1118) should not be limited to a metallic construction for these components.

V. END EFFECTORS WITH ELASTICALLY DEFORMABLE CARTRIDGE TIPS

In some instances when a straight and rigid anvil is desired, another approach to modify an end effector for enhanced visualization, maneuverability, and tissue gathering with an atraumatic tip includes the addition of an elastomeric curved tip to the distal end of a cartridge. In this manner, when end effector is closed and maneuvering to a procedure site, the added elastomeric curved tip on the distal end of cartridge fills the space that would otherwise exist at the distal end of the end effector. This configuration can reduce the drag at the distal end when maneuvering the end effector by helping to deflect tissue away from the distal end of end effector when moving the end effector through and along tissue.

Figure 29:
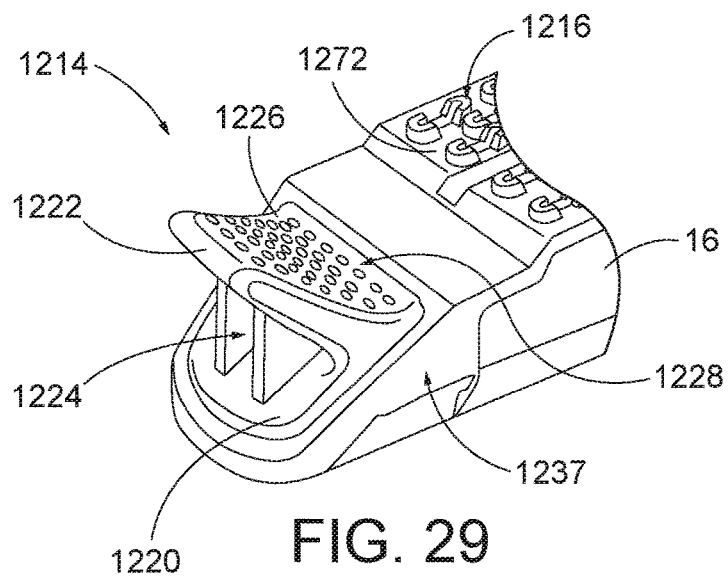
FIG. 29 depicts an enlarged perspective view of a distal portion of an exemplary alternative cartridge for an end effector for use with the surgical stapling instruments described herein.
Figure 30:
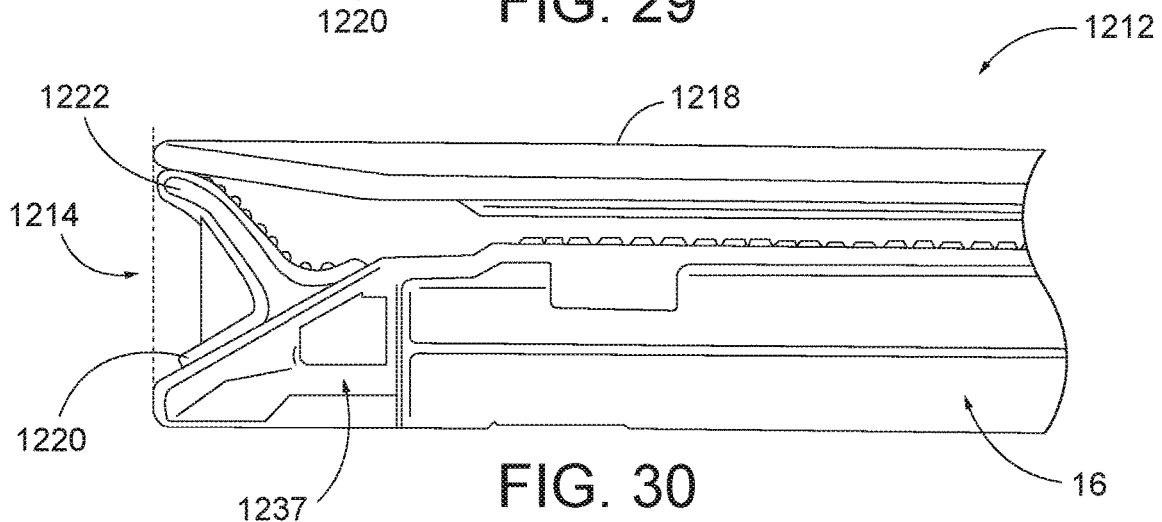
FIG. 30 depicts a side view of a distal portion of an exemplary alternative end effector having the cartridge of FIG. 29, shown without tissue capture.
Figure 31:
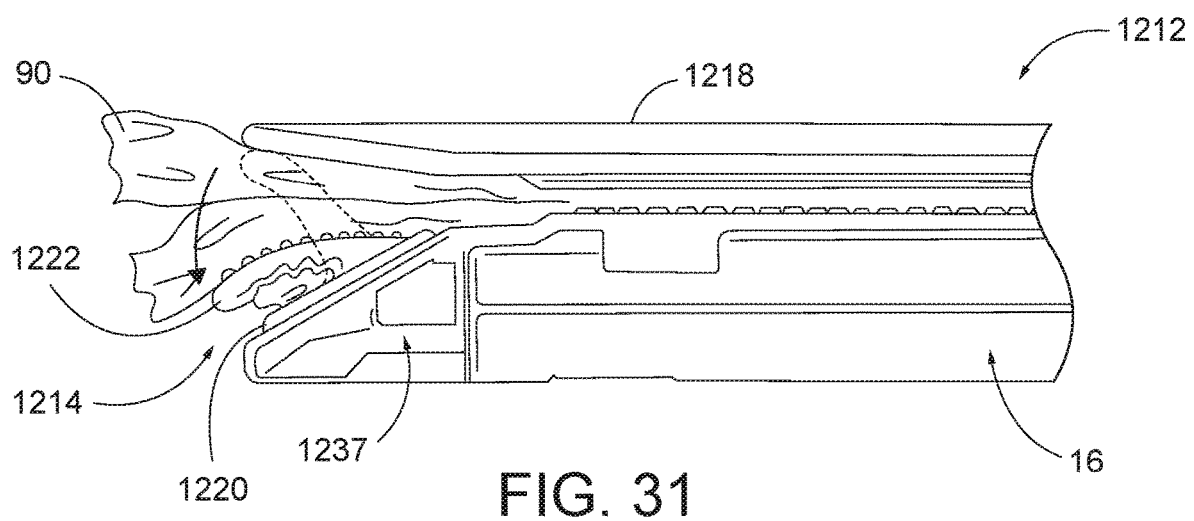
FIG. 31 depicts a side view of a distal portion of the end effector of FIG. 30, shown with tissue captured between the anvil and the cartridge.

FIGS. 29-31 show an exemplary end effector (1212) or components thereof incorporating an elastomeric curved tip (1214) attached to a distal end of a cartridge (1237). In addition to curved tip (1214) and cartridge (1237), end effector (1212) further comprises lower jaw (16) and anvil (1218). Lower jaw (16) is configured to receive cartridge (1237) in the same or similar manner as lower jaw (16) receives cartridge (37) as described above. Anvil (1218) is similar to anvil (18) described above, but with a more pointed distal end similar to anvil (218) but being straight instead of curved. Cartridge (1237) is similar to cartridge (37) as described above with a difference being the incorporation of elastomeric curved tip (1214). As shown in FIG. 29, cartridge (1237) further comprises tissue gripping features (1216) located on an upper deck (1272) of cartridge (1237). Such tissue gripping features (1216) are optional features and they may be omitted in other versions.

As mentioned above, elastomeric curved tip (1214) is attached with the angled distal end of cartridge (1237). The connection of curved tip (1214) to cartridge (1237) may be achieved using a chemical or mechanical fastening. In view of the teachings herein those of ordinary skill in the art will appreciate the various ways to connect curved tip (1214) with distal end of cartridge (1237). In some versions, curved tip (1214) is bonded to cartridge (1237) using a molding process. In such examples, distal end of cartridge (1237) may comprise various structural features configured to engage with elastomeric material of curved tip (1214) during molding to thereby secure curved tip (1214) to distal end of cartridge (1237). In the present example, curved tip (1214) is resiliently biased to extend substantially perpendicularly from the angled distal face of cartridge (1237), though it should be understood that curved tip (1214) may have any other suitable angular relationship with the angled distal face of cartridge (1237). In addition, curved tip (1214) is resiliently biased to extend along a plane that is oriented obliquely relative to the longitudinal axis of end effector (1212) in the present example.

Curved tip (1214) comprises lower lip (1220), upper lip (1222), and dividers (1224). Lower lip (1220) attaches with the angled distal end of cartridge (1237) as described above. Upper lip (1222) extends from and connects with a proximal portion of lower lip (1220). Dividers (1224) extend vertically from lower lip (1220) and connect lower lip (1220) and upper lip (1222). In the present example, upper lip (1222) comprises top surface (1226) that includes gripping features (1228) configured to improve gripping tissue clamped between anvil (1218) and cartridge (1237), for example as shown in FIG. 31.

Referring to FIGS. 30 and 31, end effector (1212) is shown in the closed position both when not clamping tissue and when clamping tissue. As shown, in the closed position in either scenario, the distal end of anvil (1218) aligns with the longitudinal position of the distal end of cartridge (1237). In other versions, end effector (1212) may be configured such that the distal end of anvil (1218) extends past cartridge (1237) when end effector (1212) is closed. Still in other versions, end effector (1212) may be configured such that the distal end of anvil (1218) terminates proximal to the distal end of cartridge (1237) when end effector (1212) is closed.

As shown in FIG. 31, when tissue (90) is captured between anvil (1218) and cartridge (1237), elastomeric curved tip (1214) deforms from its open state in FIG. 30 to a closed state as shown in FIG. 31. In this deformed state, upper lip (1222) deflects downwardly toward lower lip (1220). Furthermore, dividers (1224) are compressed and deflect laterally. As shown in FIG. 31, in its deformed state, upper lip (1222) of curved tip (1214) extends distally of anvil (1218) and cartridge (1237). With tissue clamped between end effector (1212) a cutting and stapling sequence can now occur with end effector (1212) in a similar manner to that described above with respect to end effector (12). When the clamping force is released, curved tip (1214) may resiliently return to the configuration and orientation shown in FIGS. 29-30.

In view of the teachings herein, it will be appreciated that end effector (1212) may be used in place of any of the other end effectors described herein. For instance, end effector (1212) may be used in place of end effector (12) shown in FIG. 1, or in place of end effector (312) shown in FIG. 11. In some versions, end effector (1212) may be integrally formed with either shaft (22, 322) or alternatively may be separately formed and then combined. In some versions, end effector (1212) may be provided for use in robotic systems as described above.

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a cartridge configured to hold one or more staples, (ii) an anvil movable relative to the cartridge between an open position and a closed position, and (iii) a curved distal tip located at a distal end of the cartridge or the anvil, wherein the curved distal tip comprises an elastically deformable portion configured to deflect at least a portion of the curved distal tip in response to a clamping force applied to the curved distal tip.

Example 2

The apparatus of Example 1, wherein the curved distal tip is biased to maintain a non-deformed state when the curved distal tip is not subject to the clamping force.

Example 3

The apparatus of any one or more of Examples 1 through 2, wherein the curved distal tip comprises an underside surface that defines a first plane when the curved distal tip is in a non-deformed state, wherein a first angle is defined by intersection of the longitudinal axis with the first plane, wherein the underside surface defines a second plane when the curved distal tip is in a deformed state, wherein a second angle is defined by intersection of the longitudinal axis with the second plane.

Example 4

The apparatus of Example 3, wherein the first angle is in a range of about 20 degrees to about 50 degrees in a downward direction toward the cartridge, and wherein the second angle is in a range of about 10 degrees to about 30 degrees in an upward direction away from the cartridge.

Example 5

The apparatus of any one or more of Examples 3 through 4, wherein the curved distal tip is configured to move through a range of motion from elastic deformation in a range of about 30 degrees to about 80 degrees.

Example 6

The apparatus of any one or more of Examples 1 through 5, wherein the curved distal tip of the anvil comprises a rigid portion extending distally from a body of the anvil, wherein the elastically deformable portion is overmolded onto the rigid portion.

Example 7

The apparatus of Example 6, wherein the rigid portion comprises an opening extending through the rigid portion, wherein material of the elastically deformable portion is located in the opening.

Example 8

The apparatus of any one or more of Examples 1 through 7, wherein the curved distal tip of the anvil comprises one or more tissue stabilizing features located on an underside surface of the curved distal tip.

Example 9

The apparatus of any one or more of Examples 1 through 8, wherein the curved distal tip of the anvil comprises a first engaging feature, wherein the cartridge comprises a second engaging feature, wherein the first and the second engaging features are configured to engage to provide an interlocking feature for the end effector.

Example 10

The apparatus of Example 9, wherein the first engaging feature comprises a latch connected with an underside surface of the curved distal tip, and wherein the second engaging feature comprises a recess formed a distal end of the cartridge.

Example 11

The apparatus of Example 10, wherein the latch comprises a hook member, wherein the recess comprises an undercut feature, wherein the hook member is configured to selectively engage with the undercut feature.

Example 12

The apparatus of Example 11, wherein the hook member and the undercut feature are oriented longitudinally relative to the anvil and the cartridge.

Example 13

The apparatus of Example 11, wherein the hook member and the undercut feature are oriented transversely relative to the anvil and the cartridge.

Example 14

The apparatus of any one or more of Examples 1 through 13, wherein the curved distal tip of the anvil comprises a gap setting feature configured to maintain a desired spacing between an underside surface of the curved distal tip and the cartridge when the anvil is closed.

Example 15

The apparatus of any one or more of Examples 1 through 14, wherein the cartridge comprises a distally presented surface, wherein the distally presented surface of the cartridge is oriented obliquely relative to a longitudinal axis defined by the end effector, wherein the curved distal tip extends distally from the distally presented surface of the cartridge.

Example 16

An apparatus, comprising: (a) a body; (b) a shaft extending from the body, wherein the shaft defines a longitudinal axis; and (c) an end effector in communication with the shaft, wherein the end effector is operable to compress, staple, and cut tissue, wherein the end effector comprises: (i) a cartridge configured to hold one or more staples, and (ii) an anvil movable between an open position and a closed position, wherein the anvil comprises a curved distal tip, wherein the curved distal tip comprises an elastically deformable portion configured to deflect at least a portion of the curved distal tip in response to a clamping force applied to the curved distal tip, and wherein the curved distal tip comprises a rigid distal end operably configured for tissue dissection.

Example 17

The apparatus of Example 16, wherein the curved distal tip comprises a nose portion connecting to and extending from a body of the anvil, and further connecting to the rigid distal end, wherein the curved distal tip further comprises an elastomeric member connected with the nose portion.

Example 18

The apparatus of any one or more of Examples 16 through 17, wherein the curved distal tip comprises a nose portion connecting to and extending from a body of the anvil, and further connecting to the rigid distal end, wherein the nose portion comprises a plurality of notches decreasing in size as the nose portion extends distally, wherein the plurality of notches are configured to receive elastomeric material overmolded with the nose portion.

Example 19

The apparatus of any one or more of Examples 16 through 18, wherein the curved distal tip comprises a nose portion connecting to a connection member of the anvil, and further connecting to the rigid distal end, wherein the connection member comprises a narrow width relative to the adjacent nose portion and the adjacent body of the anvil, wherein the connection member further comprises a slot extending from an end of the connection member to an opposing end of the connection member.

Example 20

An apparatus comprising: (a) a body; and (b) an end effector in communication with the body, the end effector comprising: (i) an anvil, (ii) a lower jaw, wherein the anvil is movable toward the lower jaw, and (ii) a cartridge removably received in the lower jaw, wherein the cartridge is operable to drive staples toward the anvil, wherein the cartridge comprises a distal end and an elastically deformable curved tip connected with the distal end, wherein the elastically deformable curved tip comprises a deformable upper lip, a deformable divider connected with the upper lip at a first end of the divider, and a lower lip connected with the divider at a second end of the divider.

VII. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that the teachings herein may be readily combined with various teachings in U.S. patent application Ser. No. 29/594,332, entitled "Surgical Stapler End Effector with Varying Deck Height and Tissue Gripping Features," filed on Feb. 17, 2017, issued as U.S. Pat. No. D836,198 on Dec. 18, 2018, the disclosure of which is incorporated by reference herein. Various suitable ways in which the teachings herein may be combined with the teachings of U.S. patent application Ser. No. 29/594,332, filed on Feb. 17, 2017, issued as U.S. Pat. No. D836,198 on Dec. 18, 2018, wwill be apparent to those of ordinary skill in the art.

It should also be understood that the teachings herein may be readily combined with various teachings in U.S. patent application Ser. No. 29/594,335, entitled "Circular Surgical Stapler End Effector with Varying Deck Height and Tissue Gripping Features," filed on Feb. 17, 2017, issued as U.S. Pat. No. D833,010 on Nov. 6, 2018, the disclosure of which is incorporated by reference herein. Various suitable ways in which the teachings herein may be combined with the teachings of U.S. patent application Ser. No. 29/594,335, filed on Feb. 17, 2017, issued as U.S. Pat. No. D833,010 on Nov. 6, 2018, will be apparent to those of ordinary skill in the art.

It should also be understood that the teachings herein may be readily combined with various teachings in U.S. patent application Ser. No. 15/435,607, entitled "Surgical Stapler with Insertable Distal Anvil Tip," filed on Feb. 17, 2017, issued as U.S. Pat. No. 10,729,434 on Aug. 4, 2020, the disclosure of which is incorporated by reference herein.

Various suitable ways in which the teachings herein may be combined with the teachings of U.S. patent application Ser. No. 15/435,607, filed Feb. 17, 2017, issued as U.S. Pat. No. 10,729,434 on Aug. 4, 2020, will be apparent to those of ordinary skill in the art.

It should also be understood that the teachings herein may be readily combined with various teachings in U.S. patent application Ser. No. 15/435,618, entitled "Surgical Stapler with Cooperating Distal Tip Features on Anvil and Staple Cartridge," filed on Feb. 17, 2017, published as U.S. Pub. No. 2018/0235611 on Aug. 23, 2018, the disclosure of which is incorporated by reference herein. Various suitable ways in which the teachings herein may be combined with the teachings of U.S. patent application Ser. No. 15/435,618, filed on Feb. 17, 2017, published as U.S. Pub. No. 2018/0235611 on Aug. 23, 2018, will be apparent to those of ordinary skill in the art.

It should also be understood that the teachings herein may be readily combined with various teachings in U.S. patent application Ser. No. 29/594,340, entitled "Surgical Stapler with Bent Anvil Tip and Angled Staple Cartridge Tip," filed on Feb. 17, 2017, issued as U.S. Pat. No. D836,199 on Dec. 18, 2018, the disclosure of which is incorporated by reference herein. Various suitable ways in which the teachings herein may be combined with the teachings of U.S. patent application Ser. No. 29/594,340, filed on Feb. 17, 2017, issued as U.S. Pat. No. D836,199 on Dec. 18, 2018, will be apparent to those of ordinary skill in the art.

It should also be understood that the teachings herein may be readily combined with various teachings in U.S. patent application Ser. No. 15/435,631, entitled "Surgical Stapler with Bent Anvil Tip, Angled Staple Cartridge Tip, and Tissue Gripping Features," filed on Feb. 17, 2017, issued as U.S. Pat. No. 10,758,231 on Sep. 1, 2020, the disclosure of which is incorporated by reference herein. Various suitable ways in which the teachings herein may be combined with the teachings of U.S. patent application Ser. No. 15/435,631, filed on Feb. 17, 2017, issued as U.S. Pat. No. 10,758,231 on Sep. 1, 2020, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body;
   (b) a shaft extending from the body, wherein the shaft defines a longitudinal axis; and
   (c) an end effector in communication with the shaft, wherein the end effector is operable to compress, staple, and cut tissue, wherein the end effector comprises:
      (i) a cartridge configured to hold one or more staples,
      (ii) an anvil movable relative to the cartridge between an open position and a closed position,
      (iii) a connection member extending distally from a distal end of a body of one of the cartridge or the anvil, and
      (iv) a curved rigid distal tip located at a distal end of connection member,
   wherein the connection member has a thinned profile relative to adjacent portions of the curved rigid distal tip and the body of the one of the cartridge or the anvil,
   wherein the connection member is configured to elastically deform to enable deflection of the curved rigid distal tip relative to the longitudinal axis in response to a clamping force applied to the curved rigid distal tip.

2. The apparatus of claim 1, wherein the curved rigid distal tip is biased to maintain a non-deflected state when the curved rigid distal tip is not subject to the clamping force.

3. The apparatus of claim 1, wherein the curved rigid distal tip comprises an underside surface that defines a first plane when the curved rigid distal tip is in a non-deflected state, wherein a first angle is defined by intersection of the longitudinal axis with the first plane, wherein the underside surface defines a second plane when the curved rigid distal tip is in a deflected state, wherein a second angle is defined by intersection of the longitudinal axis with the second plane.

4. The apparatus of claim 3, wherein the first angle is in a range of about 20 degrees to about 50 degrees in a downward direction toward the cartridge, and wherein the second angle is in a range of about 10 degrees to about 30 degrees in an upward direction away from the cartridge.

5. The apparatus of claim 3, wherein the curved rigid distal tip is configured to move through a range of motion from elastic deformation in a range of about 30 degrees to about 80 degrees.

6. The apparatus of claim 1, wherein the curved rigid distal tip comprises one or more tissue stabilizing features located on an underside surface of the curved rigid distal tip.

7. The apparatus of claim 1, wherein the connection member extends distally from a distal end of a body of the anvil, wherein the curved rigid distal tip comprises a first engaging feature, wherein the cartridge comprises a second engaging feature, wherein the first and the second engaging features are configured to engage to provide an interlocking feature for the end effector.

8. The apparatus of claim 7, wherein the first engaging feature comprises a latch connected with an underside surface of the curved rigid distal tip, and wherein the second engaging feature comprises a recess formed a distal end of the cartridge, wherein the latch comprises a hook member, wherein the recess comprises an undercut feature, wherein the hook member is configured to selectively engage with the undercut feature.

9. The apparatus of claim 8, wherein the hook member and the undercut feature are oriented longitudinally relative to the anvil and the cartridge.

10. The apparatus of claim 8, wherein the hook member and the undercut feature are oriented transversely relative to the anvil and the cartridge.

11. The apparatus of claim 1, wherein the curved rigid distal tip comprises a gap setting feature configured to maintain a desired spacing between an underside surface of the curved rigid distal tip and the cartridge when the anvil is closed.

12. The apparatus of claim 1, wherein the cartridge comprises a distally presented surface, wherein the distally presented surface of the cartridge is oriented obliquely relative to a longitudinal axis defined by the end effector, wherein the curved rigid distal tip extends distally from the distally presented surface of the cartridge.

13. The apparatus of claim 1, wherein the connection member includes a longitudinal slot extending distally along the longitudinal axis, wherein the longitudinal slot is configured to further promote elastic deformation of the connection member.

14. The apparatus of claim 13, wherein the longitudinal slot extends along a midline of the connection member.

15. An apparatus, comprising:
(a) a body;
(b) a shaft extending from the body, wherein the shaft defines a longitudinal axis; and
(c) an end effector in communication with the shaft, wherein the end effector is operable to compress, staple, and cut tissue, wherein the end effector comprises:
  (i) a cartridge configured to hold one or more staples, and
  (ii) an anvil movable between an open position and a closed position, wherein the anvil comprises an anvil body and a curved distal tip, wherein the curved distal tip comprises:
    (A) an elastically deformable portion extending distally from a distal end of the anvil body, and
    (B) a rigid distal portion extending distally from a distal end of the elastically deformable portion, wherein the rigid distal portion is configured to deflect relative to the anvil body about the elastically deformable portion in response to a clamping force applied to the curved distal tip, and wherein the rigid distal portion is operably configured for tissue dissection.

16. The apparatus of claim 15, wherein the rigid distal portion comprises a plurality of notches decreasing in size as the rigid distal portion extends distally, wherein the plurality of notches are configured to receive elastomeric material overmolded onto the rigid distal portion.

17. The apparatus of claim 15, wherein the elastically deformable portion comprises a narrow width relative to an adjacent portion of the rigid distal portion and an adjacent portion of the anvil body, wherein the elastically deformable portion further comprises a slot extending from an end of the elastically deformable portion to an opposing end of the elastically deformable portion.

18. The apparatus of claim 15, wherein the rigid distal portion includes a projection extending towards the cartridge and configured to first contact tissue when the anvil is moved from the open position to the closed position.

19. An apparatus comprising:
(a) a body;
(b) a shaft extending distally from the body, wherein the shaft defines a longitudinal axis; and
(c) an end effector coupled to the shaft, wherein the end effector comprises:
  (i) an anvil including:
    (A) a n anvil body,
    (B) a flexible connection member integrally connected with and extending distally from a distal end of the anvil body, wherein the flexible connection member has a narrowed width relative to the anvil body, and
    (C) a curved rigid distal tip extending distally from the flexible connection member, wherein the flexible connection member is configured to enable deflection of the curved rigid distal tip relative to the longitudinal axis in response to a clamping force applied to the curved rigid distal tip, and
  (ii) a lower jaw configured to receive a staple cartridge, wherein the anvil is movable toward the lower jaw to clamp tissue.

20. The apparatus of claim 19, wherein the flexible connection member includes a longitudinal slot extending along a midline of the flexible connection member.

* * * * *